(12) United States Patent
Thiriot et al.

(10) Patent No.: US 9,573,811 B2
(45) Date of Patent: Feb. 21, 2017

(54) METHOD FOR PREPARATION OF ALUMINUM HYDROXYPHOSPHATE ADJUVANT

(71) Applicant: Merck Sharp & Dohme Corp., Rahway, NJ (US)

(72) Inventors: David S. Thiriot, Harleysville, PA (US); Patrick L. Ahl, Yardley, PA (US); Jayme Cannon, Gaithersburg, MD (US); Gabriel M. Lobel, Telford, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 52 days.

(21) Appl. No.: 14/359,840

(22) PCT Filed: Nov. 19, 2012

(86) PCT No.: PCT/US2012/065741
§ 371 (c)(1),
(2) Date: May 21, 2014

(87) PCT Pub. No.: WO2013/078102
PCT Pub. Date: May 30, 2013

(65) Prior Publication Data
US 2014/0314653 A1    Oct. 23, 2014

Related U.S. Application Data

(60) Provisional application No. 61/563,213, filed on Nov. 23, 2011.

(51) Int. Cl.
*C01B 25/36*     (2006.01)
*A61K 39/39*     (2006.01)
*A61K 39/00*     (2006.01)

(52) U.S. Cl.
CPC ............... *C01B 25/36* (2013.01); *A61K 39/39* (2013.01); *A61K 2039/55505* (2013.01)

(58) Field of Classification Search
None
See application file for complete search history.

(56) References Cited

U.S. PATENT DOCUMENTS

2009/0016946 A1* 1/2009 Khandke ................. C01B 25/36
                                                      423/311
2011/0195086 A1* 8/2011 Caulfield ............. A61K 39/092
                                                      424/197.11

FOREIGN PATENT DOCUMENTS

WO    WO2009009629 A1    1/2009
WO    WO2010131111 A1    11/2010

OTHER PUBLICATIONS

Pall, Diafiltration: A Fast, Efficient Method for Desalting, or Buffer Exchange of Biological Samples, (2003) available at http://www.pall.com/pdfs/Laboratory/02.0629_Buffer_Exchange_STR.pdf.*

(Continued)

*Primary Examiner* — Anthony J Zimmer
(74) *Attorney, Agent, or Firm* — Henry P. Wu; Gloria M. Fuentes

(57) ABSTRACT

The present invention relates to methods for preparing amorphous aluminum hydroxyphosphate. An aluminum salt and a phosphate solution are co-mixed at a constant ratio in the presence of a buffer. Preferably, an excess of the phosphate solution is used to act as a buffer. Due to the presence of a buffer, the pH is maintained constant during reaction (after initial rapid equilibration) without active adjustment. The methods are particularly applicable for the large scale manufacturing of aluminum phosphate adjuvant. Aluminum phosphate is used as an adjuvant in vaccine formulations, particularly those including a protein or saccharide antigen.

14 Claims, 7 Drawing Sheets

(56) References Cited

OTHER PUBLICATIONS

Burrell et al., Aluminium phosphate adjuvants prepared by precipitation at constant pH. Part II: physicochemical properties, Vaccine, 2001, pp. 282-287, 19.
Burrell et al., Aluminium phosphate adjuvants prepared by precipitation atconstant pH. Part I: composition and structure, Vaccine, 2001, pp. 275-281, 19.
Klein et al., Analysis of Aluminum Hydroxyphosphate Vaccine, Journal of Pharmaceutical Sciences, 2000, 311-21, 89(3).
Johnson et al., Chemical Processing and Micromixing in Confined Impinging Jets, AIChE Journal, 2003, pp. 2264-2282, 9.
Mahajan et al., Micromixing Effects in a Two-Impinging-Jets Precipitator, AIChE Journal, 1996, pp. 1801-1814, 7.
Saso et al., The Use of High Performance Electrophoresis Chromatography for the Micropurification of Cerebrospinal Fluid Proteins in the Rat, Anal. Biochem., 1993, Issue 2, pp. 315-324, 212.
Yau et al., Aluminum Hydroxide Adjuvant Produced underConstant Reactant Concentration, Journal of Pharmaceutical Sciences, 2006, No. 8, pp. 1822-1833, 95.

\* cited by examiner

_(12) United States Patent US 9,573,811 B2_

METHOD FOR PREPARATION OF ALUMINUM HYDROXYPHOSPHATE ADJUVANT

FIELD OF THE INVENTION

The present invention relates to methods for preparing amorphous aluminum hydroxyphosphate by maintaining a constant phosphate/aluminum (P/Al) molar ratio and pH throughout the entire reaction. The methods are particularly applicable for the large scale manufacturing of aluminum hydroxyphosphate adjuvant. Aluminum hydroxyphosphate is typically used as an adjuvant in vaccine formulations, particularly those including protein or saccharide antigens.

BACKGROUND OF THE INVENTION

Vaccines have traditionally used complex immunogens such as inactivated viruses or bacteria to induce an immune response. Such vaccines were often associated with adverse side effects including hypersensitivity and the risk associated with incomplete inactivation. The use of subunit vaccines, such as antigen-based vaccines, has reduced the number and severity of unwanted side effects associated with vaccines produced with more complex immunogens. Subunit vaccines are generally composed of only one, or a few, proteins or polysaccharides from the target pathogen. Some vaccines may have a larger number of proteins or polysaccharides to provide immunity against a large number of related serotypes. Due to their small size and limited number of epitopes, by themselves, subunit vaccines tend to be only weakly immunogenic, often failing to induce a satisfactory immune response. To be effective, the use of subunit vaccines requires strategies to enhance immunogenicity.

One means to enhance vaccine immunogenicity is through the use of specific adjuvants. Immunological adjuvants are the component(s) of a vaccine which augment the immune response to the antigen. Precipitated aluminum salts, generically referred to, in the singular, in the field of vaccine adjuvants as an aluminum adjuvant or "alum", are the most widely used adjuvant in human vaccines. Not wishing to be bound by theory, several theories have been proposed for how aluminum adjuvants stimulate the immune system. One such theory is that aluminum adjuvant provides a depot of antigen at the site of administration, thereby providing a gradual and continuous release of antigen to stimulate antibody production. Aluminum adjuvants may also function by inducing a mild inflammation reaction at the injection site which primarily stimulates IL-4 and T-helper-2 cells that enhances IgG1 and IgE production. One common aluminum adjuvant is aluminum hydroxide (AlO (OH)) which is $Al^{+3}$ precipitated with $OH^-$. Another common aluminum adjuvant is aluminum hydroxyphosphate which is formed by precipitating $Al^{+3}$ with $PO_4$ and $OH^-$. Aluminum hydroxyphosphate ($Al(OH)_x(PO_4)_y$) does not have a fixed stoichiometry. The P/Al molar ratio in the aluminum adjuvant can range from just above 0 (similar to aluminum hydroxide) to approximately 1 (similar to aluminum phosphate). The extent and strength of antigen binding to the aluminum adjuvant is influenced by the properties of the aluminum adjuvant, particularly the chemical composition which is typically defined by the P/Al molar ratio along with the surface charge and size of the primary aluminum adjuvant particle.

Aluminum hydroxyphosphate is most commonly prepared by a batch precipitation method with three reactants: aluminum chloride (or other source of aluminum such as potassium aluminum sulfate), sodium phosphate and a base such as sodium hydroxide. During the course of a batch precipitation, the composition of the reacting mixture can change dramatically, leading to the production of adjuvant that is somewhat different from the start of the batch to the end of the batch. The result can be a heterogeneous mixture with some kind of "average" of properties. See Klein et al., 2000, J. Pharmaceutical Sciences 89:311-321. Not surprisingly, among commercially available aluminum phosphates from different suppliers, properties can vary significantly. For example, aluminum hydroxyphosphates can have molar ratios of phosphate to aluminum in the precipitated solids from significantly less than 0.9 to greater than 1. Others demonstrate poor particle size uniformity. These variations can present consistency problems for the commercial sale of vaccines.

Fed-batch precipitation at a constant pH improves this situation, but requires an active pH control feedback loop. See Burrell et al., 2001, Vaccine 19:275-281 and Burrell et al., 2001, Vaccine 19:282-287.

What is needed are more robust and reproducible methods for the manufacture of aluminum phosphate for use as an adjuvant.

SUMMARY OF THE INVENTION

The present invention provides methods for the preparation of aluminum hydroxyphosphate adjuvant in a manner that maintains relatively constant reaction conditions during the course of the process by simultaneously and continually combining the reactants during the process, i.e., by co-mixing the reactants. In one embodiment, the present invention comprises the following steps for production of aluminum hydroxyphosphate adjuvant:

(a) co-mixing a solution of dissolved aluminum salt (1) with a solution of phosphate (2) at a defined P/Al molar ratio to precipitate aluminum hydroxyphosphate adjuvant, in the presence of a buffer (3) that maintains a constant pH; and (b) buffer exchanging with a buffer exchange solution (4) to remove at least 80% of any excess phosphate (2), buffer (3), or other residual salts from the original reactants.

In certain embodiments of the invention, the solution of phosphate is selected from phosphoric acid and forms of sodium phosphate, potassium phosphate, or ammonium phosphate, and combination thereof. For example, the solution of phosphate may be sodium phosphate monobasic, sodium phosphate dibasic, sodium phosphate tribasic, phosphoric acid, potassium phosphate monobasic, potassium phosphate dibasic, potassium phosphate tribasic, ammonium phosphate monobasic, ammonium phosphate dibasic, ammonium phosphate tribasic, ammonium sodium phosphate, and combinations thereof. The solution of phosphate may have a pH from 7.4 to 12.4. In certain embodiments, a pH of 8.0 to 10.0 or 8.5 to 9.5 is preferred. In a preferred embodiment, the solution of phosphate comprises sodium phosphate dibasic.

In certain embodiments, the buffer is phosphate, histidine, arginine, lysine, pyrophosphate, HEPES, Tris, MOPS, succinate, or borate. In a preferred embodiment of the invention, the buffer (3) for the phosphate solution (2) is phosphate itself. In this case, the specified pH of the phosphate solution (2) is attained by adjusting the species and concentration of phosphate salts used to formulate the solution.

In certain embodiments of the invention, the aluminum salt is selected from aluminum chloride, potassium aluminum sulfate, aluminum ammonium sulfate, aluminum nitrate, aluminum bromide, aluminum bromate, aluminum chlorate, or aluminum iodide, and different hydrate forms of these. An exemplary aluminum salt is aluminum chloride hexahydrate.

In certain embodiments to produce aluminum hydroxyphosphate, the co-mixing involves a phosphate to aluminum molar ratio (initial reaction conditions) of 1.0 or greater, or 1.5 or greater. In more preferred embodiments to produce aluminum hydroxyphosphate with a final P/Al molar ratio in the adjuvant solids near 1.0, the co-mixing involves a reactant phosphate to aluminum molar ratio of 2.0 or greater, especially including the range of 2.0-3.5. In these embodiments, an upper limit of 4.0, 5.0, 5.5 or 6.0 may be imposed.

In certain embodiments of the invention, the aluminum hydroxyphosphate adjuvant has one or more of the following properties:

Zeta potential Point of Zero Charge (PZC) from 4.2 to 6.9, from 4.7 to 6.4, or 4.7 to 5.4;

Aggregate particle size volume median diameter (d(v,0.5) measured, e.g., by static light scattering) less than 40 microns, and more preferably from 2 to 10 microns, especially in the range of 3 to 6 microns;

pH in the range of 3.0 to 8.0, more preferably 4.5 to 7.2, and especially 4.5 to 5.5; or P/Al molar ratio measured in the final precipitated solid of 0.6-1.2; in certain embodiments 0.8-1.2 is preferred and especially the range of 0.9-1.1.

In certain embodiments, the methods of the invention further comprise performing size reduction prior to step (b) to reduce the volume median diameter (d(v,0.5)) of the aluminum adjuvant aggregates from about 10 to 40 microns to about 2 to 10 microns or 3 to 6 microns, as determined by static light scattering. The volume median diameter, d(v, 0.5), is the diameter where 50% of the distribution is above and 50% is below this diameter. Unless otherwise noted, reference to aggregate particle size refers to the volume median diameter as measured by Static Light Scattering (SLS).

The typical particle size range of the adjuvant aggregates following precipitation is from 2 to 40 microns. This particle size depends on precipitation conditions such as reactant concentration and mixing conditions. If necessary, size reduction may be performed by methods such as use of a rotor-stator mixer, vigorous mixing with an impeller, or recirculating through a pump. The size reduction step also ensures consistent aggregate particle size from batch to batch.

The final buffer exchanging step will adjust the final concentrations of osmolytes to the final desired values (those of the buffer exchange solution (4)). Preferred buffer exchange solutions include saline and histidine. In one embodiment, the buffer exchange solution for buffer exchanging (4) is saline. In one embodiment, the concentration of salt (sodium chloride) is adjusted to 0.9% w/v. This buffer exchange may be carried out by a settle/decant method or by ultrafiltration. Ultrafiltration is typically preferred since it is much faster than settle/decant. In certain embodiments, the extent of ultrafiltration buffer exchange is 4 to 15 diavolumes or 5 to 7 diavolumes In addition, the method may further comprise sterilizing the solution after step (b). Sterilizing may be performed by methods such as autoclaving or in-situ sterilization in the processing tank. One method of performing in-situ sterilization is to heat the product to a controlled temperature for a specified time by steaming the tank jacket and/or headspace. The product is rapidly cooled by recirculating chilled water, glycol, or another cooling medium through the jacket.

DETAILED DESCRIPTION OF THE INVENTION

Figure 1:
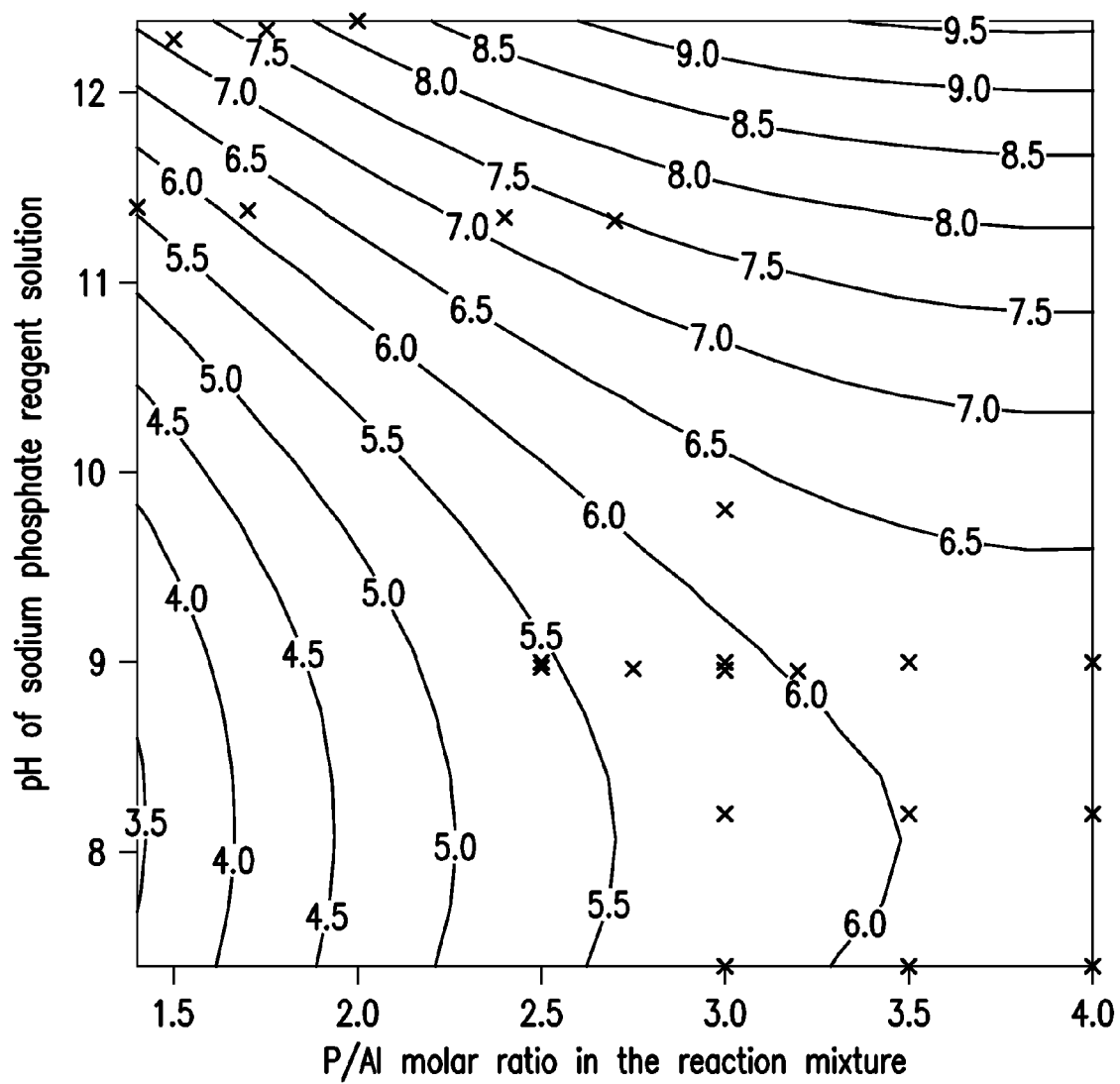
FIG. 1. pH of aluminum phosphate adjuvant (after buffer exchange, not autoclaved) as a function of pH of sodium phosphate reactant and P/Al molar ratio of the two reactant solutions. Reaction space positions of measured data points are indicated by the x symbols. Contour surface was fit using 22 data points from sample sets A and B.
Figure 2:
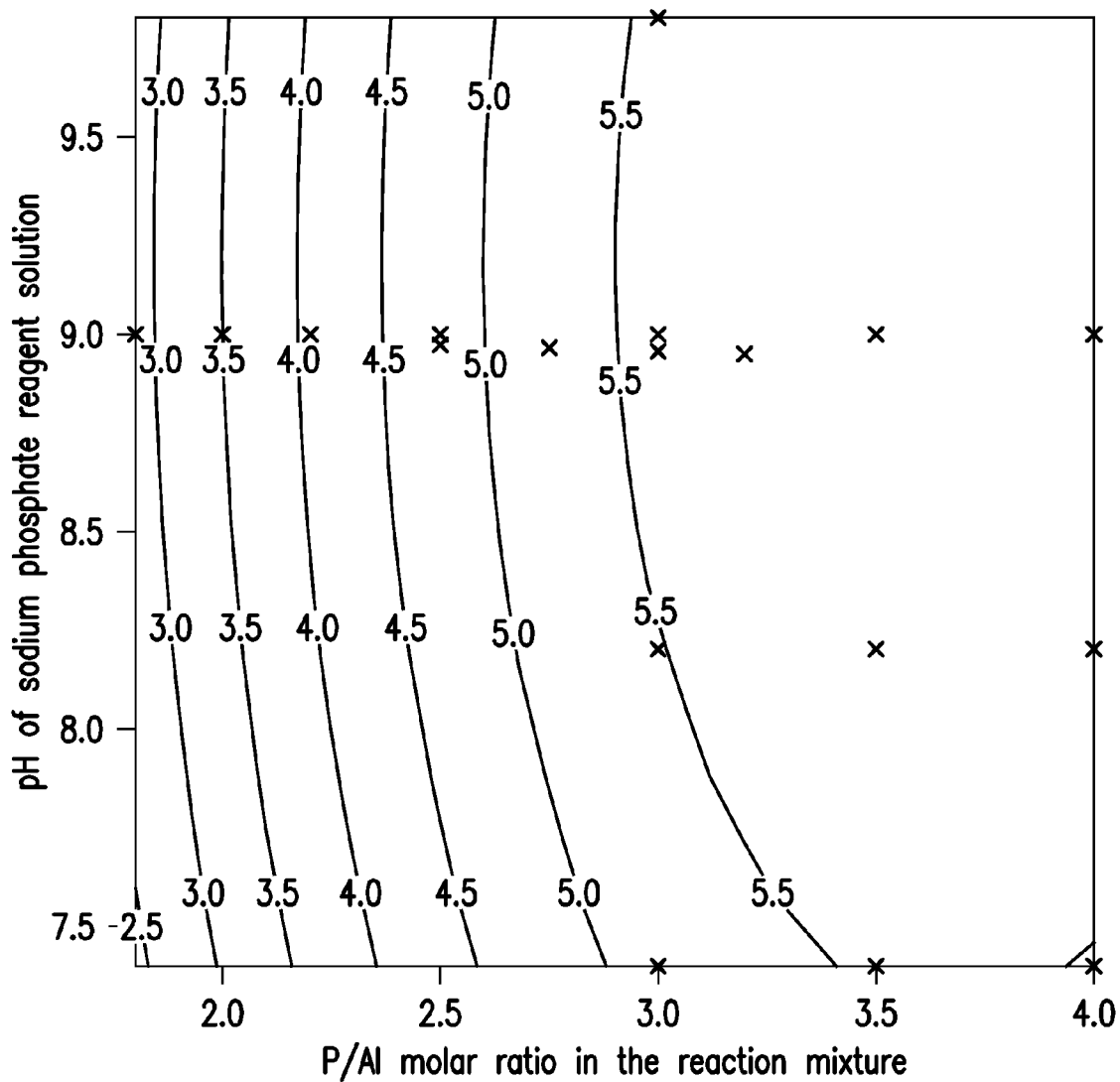
FIG. 2. pH of aluminum phosphate adjuvant (after buffer exchange, after autoclaving) as a function of pH of sodium phosphate reactant and P/Al molar ratio of the two reactant solutions. Reaction space positions of measured data points are indicated by the x symbols. Contour surface was fit using 19 data points from sample sets A, B, and C.
Figure 3:
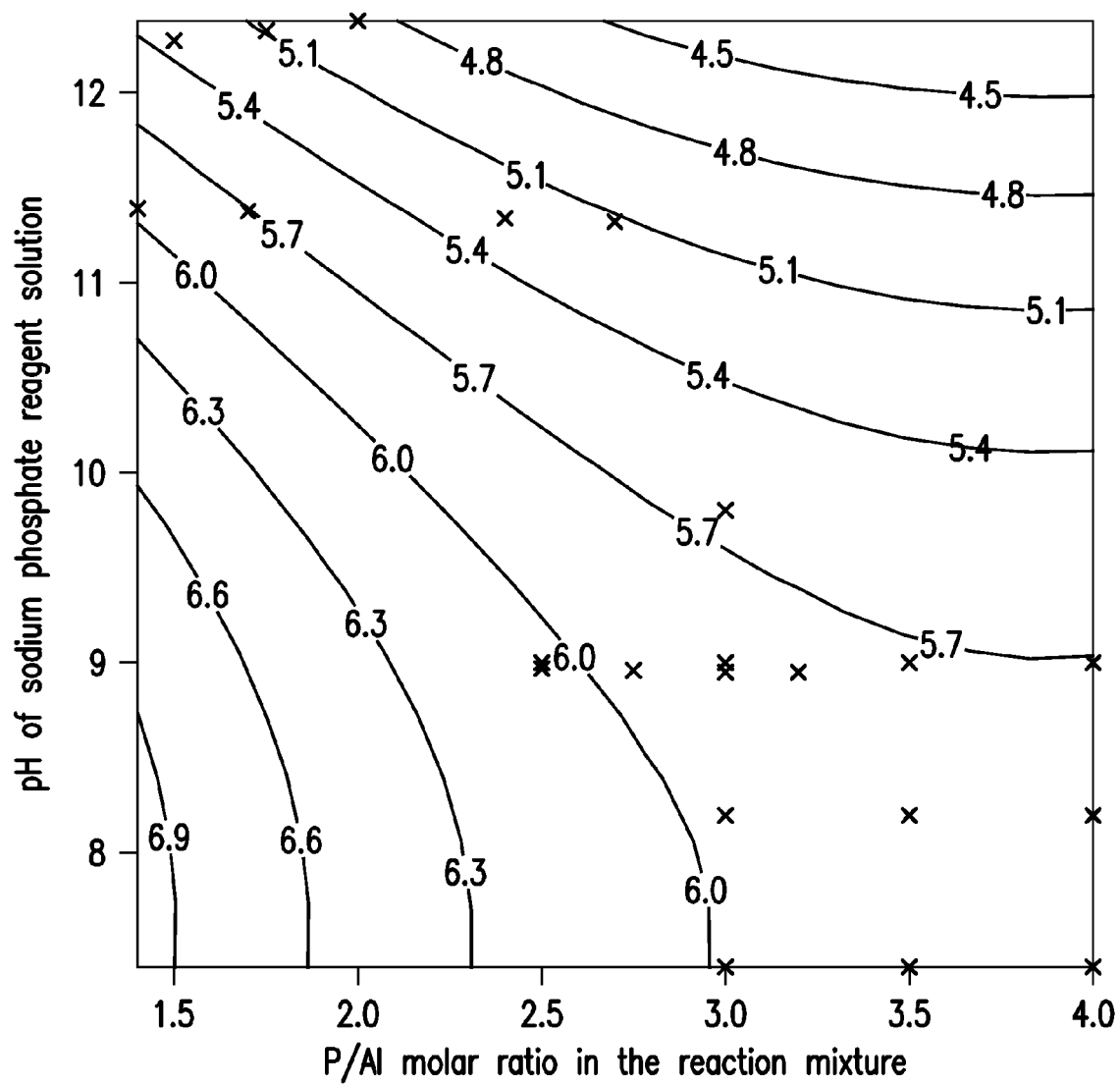
FIG. 3. PZC of aluminum phosphate adjuvant (after buffer exchange, not autoclaved) as a function of pH of sodium phosphate reactant and P/Al molar ratio of the two reactant solutions. Reaction space positions of measured data points are indicated by the x symbols. Contour surface was fit using 22 data points from sample sets A and B.
Figure 4:
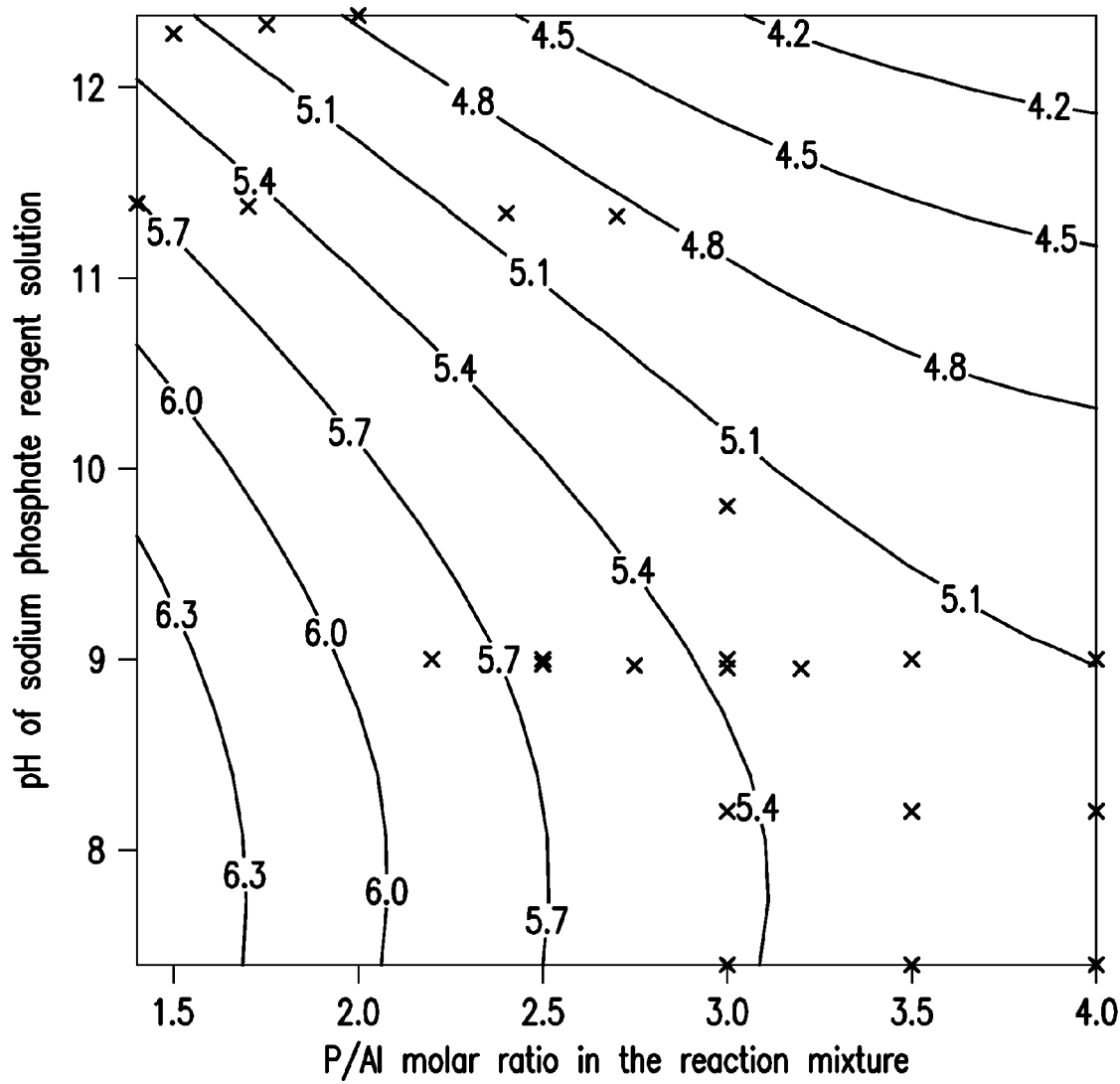
FIG. 4. PZC of aluminum phosphate adjuvant (after buffer exchange, after autoclaving) as a function of pH of sodium phosphate reactant and P/Al molar ratio of the two reactant solutions. Reaction space positions of measured data points are indicated by the x symbols. Contour surface was fit using 24 data points from sample sets A, B, and C.
Figure 5:
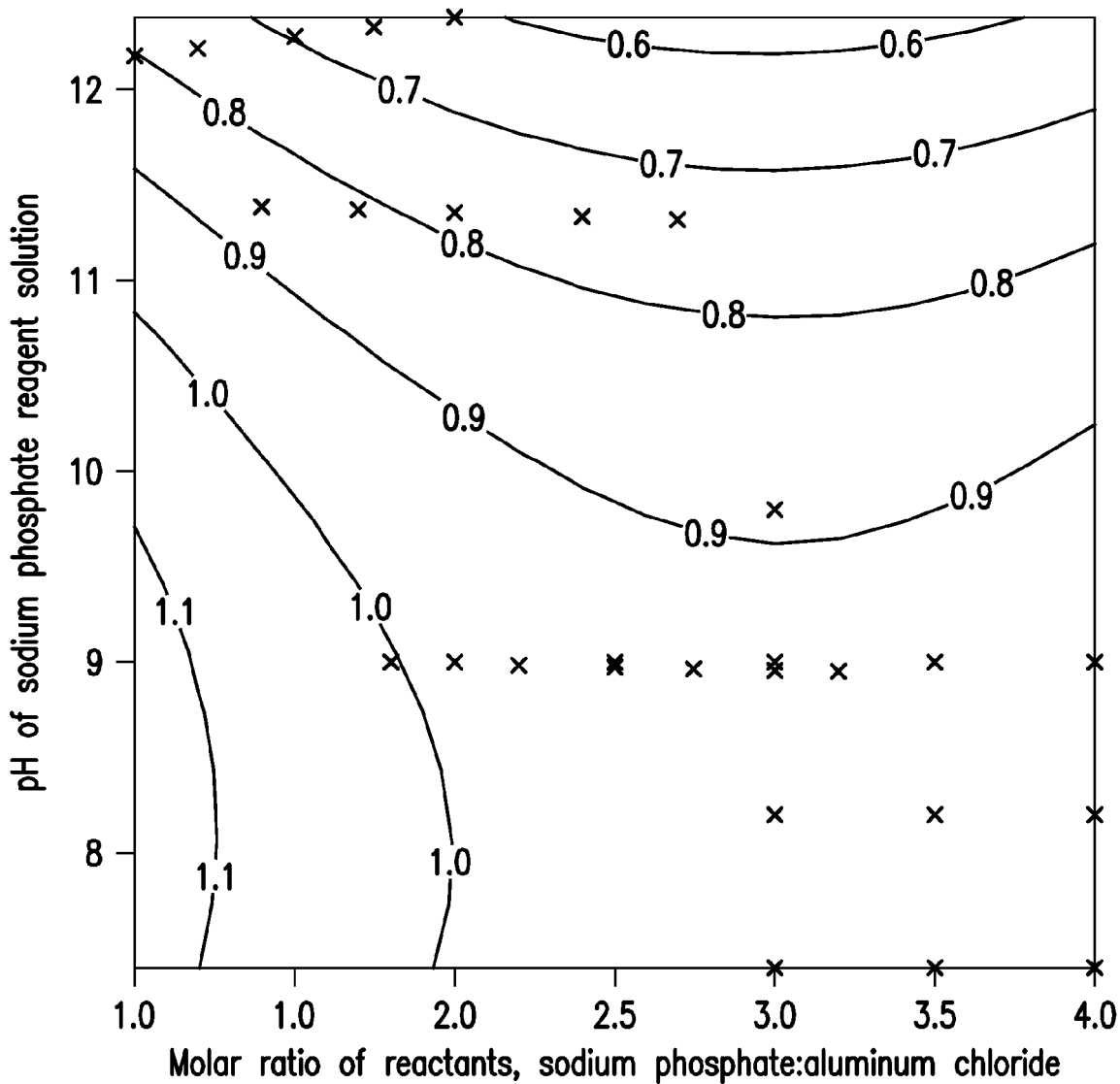
FIG. 5. P/Al molar ratio in the precipitated aluminum adjuvant solids as a function of pH of sodium phosphate reactant and P/Al molar ratio of the two reactant solutions. Reaction space positions of measured data points are indicated by the x symbols. Contour surface was fit using 34 data points from sample sets A, B, C, D, and E.

The present invention relates to methods for the preparation of aluminum hydroxyphosphate adjuvant. The invention is based, in part, on how certain parameters during the aluminum hydroxyphosphate precipitation reaction, including the molar ratio of phosphate to aluminum in the reaction and the pH at which the precipitation reaction takes place are controlled. For a general case, the pH at which the reaction takes place is controlled by the molar ratio of phosphate to aluminum in the reaction the pH and buffer capacity of a buffered solution of phosphate. For the case in which only phosphate is used without an additional buffer or buffers, the invention is based, in part, on the control of two reaction parameters: (1) the molar ratio of phosphate reactant solution to aluminum salt reactant solution; and (2) the pH of the phosphate reactant solution. Reaction space maps were used to predict how the choice of these two parameters result in final properties of the adjuvant. The methods of the invention also use "co-mixing" as a method of reactant mixing that improves manufacturing reproducibility and robustness. The methods of the invention are particularly suited for large-scale manufacture.

Some advantages of the present method over other methods include, but are not limited to, (1) the use of only two reactant streams (an aluminum salt and a phosphate solution or buffered phosphate solution), (2) constant pH maintenance during precipitation by passive means, (3) aggregate particle size control and consistency, and (4) concentration and buffer exchange via ultrafiltration.

In certain embodiments, the methods of the invention for the preparation of aluminum hydroxyphosphate adjuvant provides a convenient means of manufacturing aluminum phosphate adjuvant with the desired physical-chemical properties, and a convenient means of optimizing these properties for different intended uses, based on the choice of molar phosphate to aluminum ratio in the reaction, and the pH of the phosphate reactant solution. For example, in embodiments where co-mixing involves a phosphate to aluminum molar ratio in the reactant solutions in the range of 1.5 to 4.0 and a pH of the phosphate reactant of 7.4 to 12.4, values for certain physical-chemical parameters for the aluminum phosphate adjuvant could be controlled within the following ranges:

P/Al molar ratio in the precipitated solid: 0.6 to 1.2 (note that the P/Al molar ratio in the precipitated solid is different than the molar ratio of P/Al in the initial reacting solutions);

Zeta potential point of zero charge (PZC): 4.2 to 6.9; and pH of the precipitated solids in water or saline (without additional buffer): 3.0 to 8.0. Note, pH of the final adjuvant could be later adjusted if desired.

One reason for modulating the physical-chemical properties of the adjuvant would be enhancing the adsorption of the antigen to the adjuvant particles. Increased adsorption may be desired to enhance stability or immunogenicity of the vaccine. In cases where the mechanism of adsorption is electrostatic, the adjuvant point of zero charge helps predict the extent of adsorption at a given pH. Therefore, control of point of zero charge allows for optimization of antigen adsorption.

Another parameter that might be optimized via this method would be pH. Depending on details of the downstream vaccine formulation process, a certain pH of the adjuvant may be desirable. It is possible using the methods described to target a specific adjuvant pH without doing a separate pH adjustment later in the process.

As used herein, "maintains a constant pH" refers to the pH being held within a narrow range, e.g., ±0.10, ±0.20, or ±0.50 pH units over time after the pH has been equilibrated after the initial addition of the aluminum and solution of phosphate. The pH is maintained without any pH adjustment with, for example, NaOH.

For a given choice of reaction conditions (for example, choice of P/Al ratio in the reactant solutions, and choice of pH of the phosphate solution), the aluminum phosphate adjuvant produced by the methods of the invention would also be expected to have superior reproducibility (standard deviation lot to lot) compared to previous methods. Evidence of improved consistency in the final product for both pH and PZC is detailed in Example 2. This improvement in reproducibility may be due to the fact that a more homogenous product is precipitated during co-mixing compared to a product precipitated during a batch process.

While aluminum hydroxyphosphate adjuvant is the precise term, a commonly used term in the art for this adjuvant is aluminum phosphate adjuvant. As used herein, aluminum phosphate refers to aluminum hydroxyphosphate adjuvant.

Reactants

Preparation of aluminum phosphate adjuvant requires a source of aluminum, a source of phosphate, and enough base to allow the reaction to proceed. The final phosphate/aluminum (P/Al) ratio of the aluminum phosphate adjuvant solids controls physical-chemical and antigen binding characteristics of the adjuvant. The methods of the present invention allow for preparation of aluminum hydroxyphosphate at the desired P/Al molar ratio. In one embodiment of the invention which aims to produce a typical desired P/Al ratio, the aluminum phosphate adjuvant can have a final P/Al ratio of 0.8 to 1.2. Preferably, the final P/Al ratio is in the range of 0.9-1.1 For many vaccine applications, the typical desired target P/Al molar ratio will be approximately 1; however, this target will depend on properties of the antigen and desired extent of antigen adsorption to the adjuvant. Acceptable variability would include ±0.10, ±0.15, and ±0.20 depending on the application and precision of the assay used to measure this molar ratio.

To produce consistent, high P/Al ratio aluminum phosphate adjuvant, the competition of aluminum ligands other than phosphate should be minimized during the precipitation reaction. The other relevant competition to appreciate is between phosphate and hydroxide for binding to aluminum. P/Al ratio is maximized by performing the precipitation at lower concentrations of competing hydroxide (in other words, at lower pH) and is also enhanced by higher concentrations of phosphate. The amount of phosphate is preferably chosen to provide an excess of phosphate over aluminum. For example, the initial molar ratio of phosphate to aluminum in the reactants is from 1.5 to 4.0, preferably 2.0 to 4.0. In certain embodiments, especially preferred molar ratios are 2.0, 2.5, 3.0, and 3.5. Acceptable variability would include ±0.05, ±0.10, ±0.15, and ±0.20. The target reactant molar ratio is typically achieved by adjusting aluminum and phosphate solution concentrations and volumetric flow rates during co-mixing of the solutions. In a preferred embodiment of the invention, the volumetric flowrates of the reactants is an equal 1:1 ratio.

The source of aluminum is selected from aluminum salts, including, but not limited to, aluminum chloride hexahydrate ($AlCl_3 \cdot 6H_2O$), potassium aluminum sulfate ($KAl(SO_4)_2$) and hydrates thereof, aluminum nitrate ($Al(NO_3)_3 \cdot 9H_2O$), aluminum bromide ($AlBr_3 \cdot 6H_2O$), aluminum bromate ($Al(BrO_3)_3 \cdot 9H_2O$), aluminum chlorate ($Al(ClO_3)_3 \cdot 6H_2O$), or aluminum iodide hydrate ($AlI_3 \cdot 6H_2O$). A preferred aluminum salt is aluminum chloride (hexahydrate). The selected aluminum salt is dissolved in an appropriate volume of water.

While any form of phosphate (from $H_3PO_4$ to $PO_4^{3-}$) can be used if sufficient base is also supplied, it can be convenient and advantageous to use an excess of phosphate buffer predominantly in the dibasic form, as the single source of both phosphate and base, rather than a separate buffer. The use of co-mixing with a phosphate buffer eliminates the requirement for pH monitoring with an active feedback loop for pH control (e.g., having a reactant flow stream of sodium hydroxide, taking pH measurements during the reaction and making controlled adjustments to the sodium hydroxide reactant flow stream), providing a simpler and more robust manufacturing process. The phosphate compounds are dissolved in water and, in some embodiments, the pH of the phosphate solution adjusted to a target pH which will yield the desired characteristics in the final product. For example, a suitable amount of sodium phosphate monobasic could be added to sodium phosphate dibasic to obtain the desired pH. Suitable phosphate buffers include, but are not limited to, sodium phosphate, potassium phosphate, orthophosphoric acid ($H_3PO_4$), ammonium phosphate ($NH_4H_2PO_4$), ammonium phosphate, dibasic (($NH_4)_2HPO_4$) or other soluble alkali phosphates. A suitable pH would include any pH from 7.4 to 12.4; however, the range of 8.0 to 10.0 is preferred in certain embodiments. For example, pH 8.0, 8.5, 9.0, 9.5 or 10.0. Acceptable variability would include ±0.10, ±0.15, ±0.20, and ±0.30. In certain embodiments a pH of between 8.5 and 9.5 is especially preferred. In embodiments where a buffer together with the phosphate solution is used, suitable buffers include, but are not limited to, histidine, arginine, lysine, pyrophosphate, HEPES, Tris, MOPS, succinate, and borate. In these embodiments, the buffer would be added during formulation of the phosphate solution prior to the precipitation reaction.

In a preferred embodiment, aluminum phosphate adjuvant can be prepared by mixing appropriate concentrations of aqueous solutions of aluminum chloride (hexahydrate) and sodium phosphate, pH 9.

Precipitation

In the methods of the invention, co-mixing is used to provide a constant ratio of reactants added to the reaction. As used herein, "co-mixing" refers to any method where a constant ratio of reactants is added to the reaction vessel. By contrast, in batch precipitation, one or more reactants are added to one or more reactants already in the reaction vessel. Thus, in batch precipitation, the ratio of the reactants changes throughout the course of the reaction. Batch precipitation typically involves a solution of an aluminum salt, sodium phosphate and a base such as sodium hydroxide; one or two of what are constant throughout the reaction with the remaining added to the reaction.

Co-mixing is achieved by bringing the two reacting solutions of the aluminum salt and the phosphate buffer together at a constant rate with adequate mixing. Since the reactants are being added to a co-mixing process at a fixed constant ratio over time, a co-mixing reaction can be approximated in simple terms by time-independent parameters. Initial conditions for co-mixing aluminum phosphate reactions can be described in two dimensions: the molar ratio of phosphate to aluminum for the reactant solutions, and the pH of the sodium phosphate reactant solution. Moreover, co-mixing with a phosphate buffer provides intrinsic pH control. By proper choice of a phosphate solution that simultaneously delivers the correct amount of both phosphate and base to achieve a desired result, the reaction from start to finish occurs under approximately constant pH, without the need for feedback pH control.

The principle of co-mixing can be implemented in many different ways, with a variety of different equipment. At the lab scale, defined volumes of the two reacting solutions can be combined using syringe pumps or peristaltic pumps. It could be done with a pair of gravity flow burets or by any other means of delivering two flow streams at defined rates and mixing them. While adding the two reactants at defined, constant flow rates to a reaction vessel, rapid mixing is performed using means known in the art, such as a magnetic stirbar. At large scale, many mechanisms of delivering two defined flows (e.g., matched pumps, matched gravity feed tanks, etc.) and mixing (e.g., T-mixing, static in-line mixer, stirred tank, recirculation loop, etc.) could be used.

In one embodiment, the co-mix reaction takes place at controlled room temperature (17° C.-33° C.). Other means of temperature control could be employed, including, but not limited to, jackets and water baths.

One preferred means to achieve co-mixing is by precipitation via T-mixing. T-mixing involves tubing or piping placed in the shape of a "T". The two reactant solutions are pumped in along the horizontal axis. Flow rates are controlled. The solutions "meet" at the vertical axis and flow into the product vessel. For example, a T-mixing configuration may consist of ⅜" ID platinum-cured silicone tubing leading from each of the reactant containers through peristaltic pumps to a tubing connector "T" combining the solutions. The T-mixing apparatus may also consist of rigid metal or disposable plastic piping in a similar configuration.

During T-mixing, reactant flow rates may be, for example, in the range of approximately 300 mL/min to 5.0 L/min or 300 mL/min to 2.0 L/min. Preferred flowrate depends on the batch size being executed and materials such as tubing or piping length and diameter. For pilot scale batches, for example 5-15 L, preferred flowrates are in the range of 300 mL/min-1.2 L/min. At large scale, for example 100-500 L, faster flowrates in the range of 2.0-5.0 L/min are preferred. Appropriate flow rates and tubing diameter and length will allow for complete turbulent flow mixing of the two streams prior to entering the product vessel. In the specific case of T-mixing, mixing in the tubing is more critical than mixing in the product vessel since the precipitation reaction occurs almost instantaneously. Reynolds number can be used as a rough approximation of flow conditions in the T-mixed stream to ensure turbulent flow. Additionally, characteristic micromixing time is another useful parameter for scale-up and scale-down of such a T-mixing precipitation step. Reference can be made to Mahajan et al., 1996, AIChE Journal 7:1801-1814 and Johnson et al., 2003, AIChE Journal 9:2264-2282 for discussion of Reynolds number and characteristic micromixing time as scaling parameters for applications similar to T-mixing.

In a preferred embodiment, the reactant flow rates should be accurately and precisely controlled so that the total volume of the aluminum chloride and sodium phosphate reactants transferred to the tank is as close to 1:1 as can be reasonably achieved. Average flowrates within ±5%, ±2.5%, or ±1% of each other are generally acceptable depending on the application. This accuracy will directly relate to the aluminum concentration in the precipitated product, pH of the precipitated product, and overall consistency of the process.

For large scale precipitation using a T-mixer, the impeller in the product vessel should be turned on at the start of the precipitation process if possible to ensure the best possible mixing of the product during this step. If the impeller cannot be immediately turned on, it should be turned on as soon as possible (for example, when the liquid height in the tank reaches the bottom of the impeller blades). The precipitated intermediate is continuously mixed throughout transfer of the reactants through the T-mixer. Upon completion of reactant transfer and T-mixing, mixing is preferably continued in the tank for at least 10 to 15 minutes to ensure completion of precipitation and a homogeneous intermediate prior to the next processing step.

Particle Size Reduction

Aluminum hydroxyphosphate adjuvant consists of relatively small primary particles (10 to 120 nm discs) which form larger aggregates that can range from approximately 2 to 40 microns (d(v,0.5)) as measured by static light scattering (SLS). Controlling the particle size of the adjuvant aggregates is often important for product quality consistency and may be important for efficacy of the vaccine. Adjuvant aggregate particles below 10 micron are typically considered optimal for vaccine formulation. Since aggregate particle size is considered important, a procedure for adjusting this attribute and ensuring consistency is preferred for the method.

In one embodiment, aluminum phosphate aggregate particle size is reduced via recirculation through a high shear rotor-stator mixer. Particle size (d(v,0.5)) as measured by Static Light Scattering (SLS)) may start out >10 μm after precipitation and could be as large as about 40 μm. The size reduction unit operation will mill the particles to about 2-10

μm and more typically 3-6 μm. For example, for a large-scale process, a Silverson 275UHS High Shear Mixer with a square-hole high-shear stator can be utilized. For a small-scale process, the Silverson L4RT-A with a square-hole high-shear stator can be utilized. The following paragraphs describe the process in additional detail.

Mixing in the product vessel is continued throughout the particle size reduction process. The product is well-mixed during this step to ensure homogeneity. The product is recirculated from the tank through the high-shear mixer. At full scale, a rotary lobe pump is run during recirculation at a target flowrate which provides the desired pressure at the inlet of the high-shear mixer. In one embodiment, this flowrate is about 90 L/min. At small-scale using an L4RT-A, the high-shear mixer generates enough flow that a secondary pump is not required to facilitate recirculation. The 275UHS model mixer which may be used for this application runs at a standard speed of 3000 RPM to 3600 RPM depending on local power standards. If it is feasible, a Variable-frequency drive (VFD) is recommended to boost the mixer speed to 3600 RPM from 3000 RPM to reduce total time needed for particle size reduction. Higher rotor tip speeds generally result in significantly better size reduction efficiency with no impact to final product particle size. The small-scale L4RT-A is typically run at 8000 RPM to approximate rotor tip speed at full scale.

Temperature should be controlled near room temperature by means such as jacket of the product vessel or temperature-controlled water bath to mitigate the temperature rise that would otherwise occur due to power input from high shear mixing. Acceptable temperature range during size reduction is 17° C.-33° C.

Buffer Exchange

A concentration/diafiltration ultrafiltration step can be utilized to concentrate the product and remove the excess phosphate and other residual salts from solution which remain from the aluminum hydroxyphosphate precipitation step. Prior to diafiltration, the product is concentrated to enhance the efficiency of the diafiltration and reduce total product volume that will be sterilized and dispensed. The product is typically concentrated between 1.25× and 2.0× during this step, and preferably between 1.4× and 1.6× to ensure robustness of the diafiltration process while minimizing product volume. The product then undergoes a 4-15 diavolume diafiltration against the selected diafiltration buffer. A target of 6 diavolumes within this range has been found to minimize excessive buffer exchange while consistently achieving target free phosphate removal. A product compatible membrane with a pore size between 10 kD to 300 kD can be used for this ultrafiltration. Representative membranes that can be used include, but are not limited to, Millipore 10 kD and 300 kD Pellicon 2 Biomax (PES) V-screen Ultrafilters. If using Millipore 300 kD Pellicon 2 Biomax (PES) V-screen filters, it is recommended that retentate pressure, permeate flux, and crossflow (retentate flowrate) be controlled. Crossflow should be in the range of 710-750 Liters/(meter$^2$-hour). Permeate flux in the range of 25-38 Liters/(meter$^2$-hour), and retentate pressure controlled between 5 and 15 psig. Pressure drop (ΔP) across the filter cassette and Transmembrane Pressure (TMP) should be monitored during the process but are not controlled.

A variety of buffers could be used for the buffer exchange step depending on the desired background for the aluminum hydroxyphosphate adjuvant particles. Preferred buffers include saline and histidine. In one preferred embodiment, the solution for buffer exchanging is saline. In one embodiment, the concentration of salt (sodium chloride) is 0.9% w/v. Additional pharmaceutically acceptable excipients and/or adjuvants can be included during this step.

It is noted that a settle/decant process can also be used for buffer exchange; however, ultrafiltration is preferred since it is a much faster process.

Steam Sterilization

After completion of diafiltration, the product can be steam sterilized by means well known in the art, including autoclaving bottles of product or in-situ sterilization in the product vessel. Sterilization of the aluminum phosphate product will impact product quality attributes, most notably pH, Point-of-Zero Charge (PZC), solution (free) phosphate concentration, and P/Al molar ratio in the adjuvant solids. For some cases (P/Al molar ratio in the solids near 1), exposure to the high heat (121-130° C.) seen during steam sterilization causes the pH of the product to drop, PZC to drop, and phosphate to be liberated from the solids therefore increasing solution phosphate in the supernatant and decreasing P/Al ratio in the adjuvant solids. The extent of these changes depends on the original parameters used for the initial reactants, extent of buffer exchange, and sterilization time. As an example, the pH may drop 0.5 pH units, the PZC may drop 0.5 pH units, solution phosphate may increase from about 3-8 mM to about 13-22 mM, and P/Al ratio may drop from about 1.1 to 1.0. Change in solution (free) phosphate upon sterilization is dependent on adjuvant concentration, whereas change in pH, PZC, and P/Al ratio is much less or not at all dependent on adjuvant concentration.

Sterilization typically does not change the size of the adjuvant aggregates during a typical autoclave sterilization cycle. However, the adjuvant aggregate size has been found to significantly increase if the adjuvant suspension is allowed to cool too slowly after sterilization, for example over a 12-hour period. In this case the aggregate size has been seen to increase from 3.9 μm (d(0.5) by SLS) prior to sterilization to 11.6 μm after sterilization.

An understanding of product changes during sterilization is important, since the initial reactant conditions may be adjusted to account for these changes to successfully meet final product target characteristics. Experience has shown that the product may be steam sterilized in glass at temperatures from 122° C. to 130° C. for up to 4.3 hours and still meet acceptable product quality attributes, given that this length of sterilization is accounted for in design of the reactant conditions. Though the product may stand-up to such a lengthy sterilization cycle, minimizing heat exposure is recommended when possible. Once optimized, a typical in-situ steam sterilization cycle can be expected to heat the product to between 122° C. and 127° C. within 35 minutes, "dwell" at the sterilization set-point for between 24 and 30 minutes, and cool the product to below 30° C. within 30 minutes.

Adjuvant Properties pH

Adjuvant pH can be adjusted depending on the application of the adjuvant and the antigen in use (the stability of certain antigens is affected by pH). This adjustment can be done by manipulating the P/Al molar ratio in the reactants, modulating pH of the incoming phosphate buffer, or performing a final pH adjustment of the product prior to vaccine formulation. Generally, adjuvant pH can be 3.0 to about 8.0; in certain preferred embodiments pH values are about 4.5 to about 7.2. One especially preferred embodiment of the invention results in a pH of between 4.5 and 5.5.

Point-of-Zero Charge

The Zeta potential of aluminum adjuvant is related to the surface charge on the adjuvant particles, and will influence the adsorption of antigens that bind to the aluminum adjuvant through electrostatic interactions. One parameter used to quantify the surface charge of an aluminum adjuvant is the Point-of-Zero Charge (PZC) which is the pH where the zeta potential of the particle is zero. PZC is measured using standard methods known in the art.

Generally, adjuvant PZC is between 4.2 to 6.9; in certain preferred embodiments PZC values are about 4.7 to 6.4. One especially preferred embodiment of the invention results in a PZC of between 4.7 and 5.4.

Particle Size

Adjuvant aggregate particle size may be of importance to vaccine products. For example, aggregate particle size influences cellular uptake and may also impact immunogenic response, but this effect is likely variable depending on the antigen. In the particular application of the invention, the target aggregate particle size is 2-10 μM, and more preferably 3-6 μM.

Phosphate/Aluminum Molar Ratio

The molar ratio of Phosphate to Aluminum (P/Al molar ratio) in the adjuvant solids defines the composition of the adjuvant and impacts most of the physical characteristics such as PZC and primary particle shape/size. In particular, the effect on the PZC of the adjuvant can affect the binding properties of the antigen. The P/Al ratio also is related to the amount of hydroxyl that is coordinated to the Aluminum solids. As the ratio of Phosphate increases, the amount of hydroxyl bound to Al is expected to decrease. Generally, using the methods described here, P/Al molar ratio is between 0.6 and 1.2. One embodiment of this invention targets a P/Al molar ratio of 0.8 to 1.2 and preferably 0.9 to 1.1. The P/Al ratio may be changed to suit the specific application by adjusting the reactant conditions as discussed above.

Antigen Adsorption

The aluminum phosphate adjuvant of the invention can be combined with one or more active agents e.g., antigens, as well as additional adjuvants. In one embodiment, the active agent is mixed with and possibly adsorbed onto aluminum hydroxyphosphate adjuvant in the presence of a buffering system compatible with the specific active agent during the vaccine formulation process. Further guidance for adsorbing active agents can be found in U.S. Pat. Nos. 3,925,545 and 4,016,252, and Relyveld, 1986, Dev Biol Stand 65:131-136.

In cases where the active agent is an antigen, the antigen is preferably a protein antigen or a saccharide antigen (optionally conjugated). Preferred antigens include, but are not limited to antigens of the following bacteria: *Bacillus anthracis, Bordetella pertussis, Chlamydia pneumoniae, Chlamydia trachoniatis, Haemophilus influenzae B, Helicobacter pylori, N. gonorrhoeae, Neisseria meningitides, Staphylococcus aureus, Streptococcus agalactiae* (group B streptococcus), *Streptococcus pyogenes* (group A streptococcus), and *Streptococcus pneumoniae*. Preferred antigens also include but are not limited to antigens of the following viruses: flavivirus (such as from yellow fever virus, Japanese encephalitis virus, Dengue viruses, tick-borne encephalitis virus, West Nile virus), hepatitis A virus, hepatitis B virus, hepatitis C virus, human papillomavirus, a parvovirus (e.g., parvovirus B19), poliovirus (inactivated) and Chikungunya virus. Preferred antigens also include diphtheria toxoid and tetanus toxoid. All antigens may be recombinantly produced in other organisms by methods known in the art.

Antigens in the composition will typically be present at a concentration of at least 1 μg/ml each. In general, the concentration of any given antigen will be sufficient to elicit an immune response against that antigen.

Where a saccharide or carbohydrate antigen is used, it is preferably conjugated to a carrier protein in order to enhance immunogenicity. Preferred carrier proteins are bacterial toxins or toxoids, such as diphtheria or tetanus toxoids. The $CRM_{197}$ diphtheria toxoid is particularly preferred. Other suitable carrier proteins include the *N. meningitidis* outer membrane protein, pertussis proteins, protein D from *H. influenzae*, toxin A or B from *C. difficile*, etc.

Vaccine Compositions

The aluminum hydroxyphosphate adjuvant prepared by the methods of the present invention may be used, either as-is or adsorbed to an antigen, to formulate vaccines according to well-known practices and compositions in the art.

The formulation of vaccine compositions is generally known in the art and reference can conveniently be made to Remington's Pharmaceutical Sciences, 20th ed., Mack Publishing Co., Easton, Pa., USA.

EXAMPLES

Example 1

Screening the Aluminum Phosphate "Reaction Space" at Laboratory Scale to Identify Reaction Conditions that Result in Desirable Aluminum Phosphate Adjuvant Properties Many samples of aluminum phosphate adjuvant were prepared by a co-mixing method at laboratory scale in order to screen the reaction space and understand which reaction conditions lead to desirable aluminum phosphate adjuvant properties. The samples were not all prepared on the same occasion. The primary variables that were changed between the samples were 1) the initial phosphate/aluminum (P/Al) molar ratio of the two reactant solutions (a sodium phosphate solution and an aluminum chloride hexahydrate solution), and 2) the pH of the sodium phosphate reactant solution. (Other details of the preparations varied slightly from preparation to preparation, as will be described below, but these differences were considered of lesser consequence, and the results from samples prepared on different occasions were considered together during analysis as a single group.)

Analysis of the samples included 1) measurement of the pH, after buffer exchange but before autoclaving; 2) measurement of the pH, after buffer exchange and after autoclaving; 3) the zeta potential point of zero charge (PZC), after buffer exchange but before autoclaving; 4) the zeta potential point of zero charge after buffer exchange and after autoclaving; 5) the P/Al molar ratio in the precipitated solids, by ICP (inductively coupled plasma atomic emission spectroscopy). (Most or all of the samples measured by ICP were after buffer exchange and after autoclaving.) Not all of the samples were analyzed by all five of the above methods.

TABLE 1

Lab-scale preparations of aluminum phosphate adjuvant prepared to screen the precipitation reaction space.

| Sample set | Initial P/Al molar ratio of the reactant solutions | pH of the sodium phosphate reactant solution | pH after buffer exchange, before autoclaving | pH after buffer exchange, after autoclaving | PZC after buffer exchange, before autoclaving | PZC after buffer exchange, after autoclaving | P/Al molar ratio in the precipitated solids |
|---|---|---|---|---|---|---|---|
| A | 1.50 | 12.28 | 7.24 |  | 5.00 | 4.90 | 0.72 |
| A | 1.75 | 12.33 | 7.96 |  | 4.97 | 4.94 | 0.63 |
| A | 2.00 | 12.38 | 8.45 |  | 5.24 | 5.13 | 0.51 |
| A | 2.50 | 8.97 | 5.56 | 5.04 | 6.03 | 5.57 | 0.88 |
| A | 2.75 | 8.96 | 5.88 | 5.39 | 5.89 | 5.36 | 0.84 |
| A | 3.00 | 8.96 | 6.02 | 5.56 | 5.80 | 5.25 | 0.86 |
| A | 3.20 | 8.95 | 6.10 | 5.66 | 5.73 | 5.22 | 0.89 |
| A | 1.40 | 11.39 | 5.21 |  | 6.21 | 5.81 | 0.90 |
| A | 1.70 | 11.38 | 6.13 |  | 5.68 | 5.29 | 0.86 |
| A | 2.40 | 11.34 | 6.83 |  | 5.21 | 4.98 | 0.83 |
| A | 2.70 | 11.32 | 7.17 |  | 4.98 | 4.83 | 0.80 |
| B | 3.00 | 7.4[†] (7.40)[‡] | 5.63 | 5.12 | 6.05 | 5.41 | 0.94 |
| B | 3.00 | 8.2[†] (8.23)[‡] | 6.00 | 5.53 | 5.83 | 5.28 | 1.00 |
| B | 3.00 | 9.0[†] (8.99)[‡] | 6.02 | 5.62 | 5.85 | 5.22 | 1.01 |
| B | 3.50 | 7.4[†] (7.40)[‡] | 5.83 | 5.38 | 5.94 | 5.30 | 1.03 |
| B | 3.50 | 8.2[†] (8.24)[‡] | 6.13 | 5.76 | 5.81 | 5.20 | 0.85 |
| B | 3.50 | 9.0[†] (8.95)[‡] | 6.17 | 5.81 | 5.81 | 5.18 | 0.98 |
| B | 4.00 | 7.4[†] (7.41)[‡] | 6.06 | 5.67 | 5.86 | 5.24 | 1.01 |
| B | 4.00 | 8.2[†] (8.24)[‡] | 6.20 | 5.83 | 5.77 | 5.19 | 1.00 |
| B | 4.00 | 9.0[†] (8.95)[‡] | 6.27 | 5.89 | 5.71 | 5.15 | 0.96 |
| B | 2.50 | 9.0[†] (8.98)[‡] | 5.51 | 5.00 | 6.07 | 5.57 | 1.00 |
| B | 3.00 | 9.8[†] (9.91)[‡] | 6.01 | 5.59 | 5.87 | 5.33 | 0.87 |
| C | 1.80 | 9.00 | 4.02 | 2.90 |  |  | 0.97 |
| C | 2.00 | 8.99 | 4.18 | 3.17 |  |  | 1.01 |
| C | 2.20 | 8.98 | 4.96 | 4.12 |  | 6.25 | 1.00 |
| C | 2.50 | 8.97 | 5.56 | 4.88 |  | 5.77 | 1.00 |
| D | 1.00 | 12.18 | 4.92 | 4.18 |  |  | 0.81 |
| D | 1.20 | 12.22 | 5.91 | 5.56 |  |  | 0.72 |
| D | 2.00 | 11.36 | 6.06 | 5.71 |  |  | 0.81 |
| E | 2.20 | 8.98 | 4.82 |  |  |  | 0.93 |
| E | 2.20 | 8.98 | 4.83 |  |  |  | 0.93 |
| E | 2.20 | 8.98 | 4.82 |  |  |  | 0.95 |
| E | 2.20 | 8.98 | 4.82 |  |  |  | 0.95 |
| E | 2.20 | 8.98 | 4.80 |  |  |  | 0.97 |

[†]Target value, used for FIGS. 1-5 below.
[‡]Measured value.

For the purpose of understanding the reaction space and how to achieve desired properties in the aluminum phosphate adjuvant, it was convenient to visualize the data by fitting with mathematically calculated surfaces and displaying as contour plots (see FIGS. 1-5).

Preparation details for each of the 5 sample sets (A, B, C, D, and E) are as follows.

Set A

Set A samples were prepared by mixing equal volumes of aluminum chloride hexahydrate solution and sodium phosphate solution, such that the final concentration of aluminum after mixing would be 1.8 mg of aluminum/mL. This required preparation of a 3.6 mg/mL aluminum solution from aluminum chloride hexahydrate. (Aluminum is 26.98 grams/mol, and aluminum chloride hexahydrate is 241.43 grams/mol). The aluminum chloride hexahydrate solution was prepared by first dissolving 115.99 grams aluminum chloride hexahydrate in water (resulting in a solution that was 12.96 mg/mL in aluminum), then mixing 278 mL of that solution with 722 mL of water to give 1 L of a 3.6 mg/mL solution of aluminum. The aluminum chloride hexahydrate solution was the same for all 11 samples, while the sodium phosphate solution was different for all 11 samples. The sodium phosphate solutions were made by making dilutions and mixtures of more concentrated stock solutions of sodium phosphate dibasic and sodium phosphate tribasic. The sodium phosphate dibasic stock solution was 0.5 M. The sodium phosphate tribasic solution used for some of the samples was 0.25 M, and for other of the samples a different stock solution of sodium phosphate tribasic was used that was 0.333 M. 70 mL of each of 11 different phosphate solutions were prepared, as described in the table below.

TABLE 2

Preparation details for sample set "A".

| Target molar ratio of P:Al for the reactant solutions | Target conc. (M) of phosphate for phosphate reactant solution | Contribution to conc. (M) from sodium phosphate tribasic | Contribution to conc. (M) from sodium phosphate dibasic | Conc. (M) of stock sodium phosphate tribasic | Conc. (M) of stock sodium phosphate dibasic | Volume (mL) of stock sodium phosphate tribasic | Volume (mL) of stock sodium phosphate dibasic | Volume (mL) of water |
|---|---|---|---|---|---|---|---|---|
| 1.5 | 0.200 | 0.200 | 0 | 0.25 |  | 56.0 | 0 | 14.0 |
| 1.75 | 0.233 | 0.233 | 0 | 0.25 |  | 65.4 | 0 | 4.6 |
| 2 | 0.267 | 0.267 | 0 | 0.3333 |  | 56.0 | 0 | 14.0 |
| 2.5 | 0.334 | 0 | 0.334 |  | 0.5 | 0 | 46.7 | 23.3 |
| 2.75 | 0.367 | 0 | 0.367 |  | 0.5 | 0 | 51.4 | 18.6 |
| 3 | 0.400 | 0 | 0.400 |  | 0.5 | 0 | 56.0 | 14.0 |
| 3.2 | 0.427 | 0 | 0.427 |  | 0.5 | 0 | 59.8 | 10.2 |
| 1.4 | 0.187 | 0.093 | 0.093 | 0.25 | 0.5 | 26.2 | 13.1 | 30.8 |
| 1.7 | 0.227 | 0.113 | 0.113 | 0.25 | 0.5 | 31.8 | 15.9 | 22.4 |
| 2.4 | 0.320 | 0.160 | 0.160 | 0.25 | 0.5 | 44.8 | 22.4 | 2.8 |
| 2.7 | 0.360 | 0.180 | 0.180 | 0.3333 | 0.5 | 37.8 | 25.2 | 7.0 |

Aluminum chloride hexahydrate solution was drawn up into a 60 mL disposable plastic syringe. Sodium phosphate solution was drawn up into a different 60 mL disposable plastic syringe. A short length of silicone tubing was attached to the end of each of the syringes. The other end of each piece of tubing was attached to one or the other of two inlets at the top of a short plastic static in-line mixer (Conprotec MB6.5-16S). After passing through the in-line mixer, the mixture was collected in a beaker, which was stirred by a magnetic stir bar. The two 60 mL syringes were expelled at the same 1:1 volume ratio by placing them onto a syringe pump which accepted 2 syringes, and which pushed the two syringe plungers at the same rate with a single moving metal bar. With 60 mL in each syringe, the final volume of the mixture was 120 mL. The contents of the syringes were mixed through the static in-line mixer and into the stirred beaker in less than 6 minutes.

The lab scale buffer exchange process was conducted by adding about 1 liter of 0.9% sodium chloride solution to about 100 mL of precipitated aluminum adjuvant, mixing by hand to resuspend the aluminum adjuvant, allowing the solids to settle (often overnight), removing about 1 liter of supernatant (leaving the aluminum adjuvant solids), and repeating that process multiple times. Five rounds of this "settle/decant" procedure were conducted over a period of approximately a week to buffer exchange the samples into 0.9% sodium chloride solution.

After buffer exchange, each sample was divided into two aliquots to allow measurements to be made on samples before and after autoclaving. Autoclaving used a liquids cycle for 60 minutes at 121° C.

Set B

Set B samples were prepared in a manner similar (but not identical) to Set A samples. The same stock aluminum chloride hexahydrate solution that was used for the Set A samples was used for the Set B samples. It was diluted in the same manner. Stock solutions of 0.6 M sodium phosphate dibasic and 0.6 M sodium phosphate monobasic were prepared. For sodium phosphate dibasic (FW 141.96 g/mol), 85.172 grams was dissolved in 1 liter of water, and separately 42.591 grams was dissolved in 0.5 liters of water, giving two solutions of 0.6 M. For sodium phosphate monobasic monohydrate (FW 137.99), 82.793 grams was dissolved in water giving a solution of 0.6 M. Four pH targets for the phosphate buffer were 9.0, 8.2, 7.4, and 9.8. The pH 9 target was reached by using sodium phosphate dibasic solution alone, which gave a measured pH of 8.95-8.99. The pH targets of 8.2 and 7.4 were achieved by adding 0.6 M sodium phosphate monobasic to 0.6 M sodium phosphate dibasic. The pH target of 9.8 was achieved by starting with 0.6 M sodium phosphate dibasic solution, and adding a small volume (~2%, small phosphate dilution ignored) of 1 N sodium hydroxide solution. Using the pH adjusted 0.6 M stock sodium phosphate solutions, 11 different phosphate solutions (each with a volume of 140 mL) were prepared by dilution with water, as described in the table below.

TABLE 3

Preparation details for sample set "B".

| Target molar ratio of P:Al for the reactant solutions | Target pH for the phosphate reactant solution | Volume of pH-adjusted 0.6M sodium phosphate | Volume of water | Resulting concentration (M) of sodium phosphate reactant solution |
|---|---|---|---|---|
| 3.00 | 7.4 | 93.4 | 46.6 | 0.400 |
| 3.00 | 8.2 | 93.4 | 46.6 | 0.400 |
| 3.00 | 9.0 | 93.4 | 46.6 | 0.400 |
| 3.50 | 7.4 | 109.0 | 31.0 | 0.467 |
| 3.50 | 8.2 | 109.0 | 31.0 | 0.467 |
| 3.50 | 9.0 | 109.0 | 31.0 | 0.467 |
| 4.00 | 7.4 | 124.5 | 15.5 | 0.534 |
| 4.00 | 8.2 | 124.5 | 15.5 | 0.534 |
| 4.00 | 9.0 | 124.5 | 15.5 | 0.534 |

TABLE 3-continued

Preparation details for sample set "B".

| Target molar ratio of P:Al for the reactant solutions | Target pH for the phosphate reactant solution | Volume of pH-adjusted 0.6M sodium phosphate | Volume of water | Resulting concentration (M) of sodium phosphate reactant solution |
|---|---|---|---|---|
| 2.50 | 9.0 | 77.8 | 62.2 | 0.333 |
| 3.00 | 9.8 | 93.4 | 46.6 | 0.400 |

As for the samples of Set A, the two reactant solutions were drawn up into 60 mL syringes and were expelled at the same rate at a 1:1 volume ratio into the reaction beaker. The reaction for Set B differed from Set A in that no "T" or static in-line mixer was used. A short length of silicone tubing was attached to the end of each of the reactant solution syringes, and co-mixing was achieved as the two reactant solutions dropped into a beaker. Inside the beaker was a magnetic stirbar, which provided mixing while the reactants were being added to the beaker, and for a short time (minutes) thereafter. For each sample, the reactant solution syringes were loaded and expelled twice, which doubled the prepared volume over what was prepared for sample Set A.

Buffer exchange into 0.9% saline solution was performed in a manner similar to that done for the Set A samples, except that 6 rounds of "settle/decant" were conducted. After buffer exchange, each sample was divided into two aliquots to allow measurements to be made on samples before and after autoclaving. Autoclaving used a liquids cycle for 60 minutes at 121° C.

Set C

A single solution of aluminum chloride hexahydrate (FW 241.43 g/mol) was prepared by dissolving 19.33 grams in 600 mL of water. This resulted in a solution with the concentration of 3.6 grams aluminum/mL. Four solutions of sodium phosphate dibasic (FW 141.98 g/mol) were prepared, at four different concentrations of sodium phosphate dibasic, but without pH adjustment. The pH of the four resulting sodium phosphate dibasic solutions were all measured to be in the range of 9.00-8.97. The phosphate solutions were prepared as described in the table below.

TABLE 4

Phosphate solutions used to prepare sample set "C"

| Target molar ratio of P:Al for the reactant solutions | Amount of sodium phosphate dibasic dissolved in 150 mL water |
|---|---|
| 1.8 | 5.1223 grams |
| 2.0 | 5.6858 grams |
| 2.2 | 6.2549 grams |
| 2.5 | 7.1087 grams |

The two reactant solutions were loaded into 60 mL syringes. As in the case for Sample Set A, the reactant solutions flowed through a small plastic static in-line mixer, before the mixture dropped into a stirred beaker. As in the case for Sample Set B, for each of the 4 samples the reactant syringes were loaded and expelled twice, producing about 220 mL for each of the four samples. The flow rate was 1 mL/second for both syringes (0.5 mL/second/syringe). Rapid stirring continued for 5 minutes after the second pair of reactant syringes had been expelled. Buffer exchange included 4 cycles of settle/decant, and included a dilution step for the adjuvant from 1.8 mg aluminum/mL to 0.9 mg aluminum/mL. Measurements were made on the sample before autoclaving, and after autoclaving with a liquids cycle for 60 minutes at 121° C.

Set D

A single solution of aluminum chloride hexahydrate (FW 241.43 g/mol) was prepared by dissolving 16.1054 grams in 1 liter of water. This resulted in a solution with the concentration of 1.8 grams aluminum/mL. A stock solution (0.5 M) of sodium phosphate dibasic (FW 141.96 g/mol) was prepared by dissolving 70.98 grams sodium phosphate dibasic in 1 liter of water. A stock solution (0.25 M) of sodium phosphate tribasic dodecahydrate (FW 380.13) was prepared by dissolving 95.03 grams in 1 liter of water. To prepare the sodium phosphate reactant solutions, the sodium phosphate stock solutions were diluted and combined as indicated in the table below.

TABLE 5

Preparation details for sample set "D".

| Target molar ratio of P/Al for the reactant solutions | Concentration of aluminum in the aluminum chloride reactant solution | Concentration (mM) of sodium phosphate tribasic in the phosphate reactant solution | Concentration (mM) of sodium phosphate dibasic in the phosphate reactant solution |
|---|---|---|---|
| 1.00 | 66.7 mM | 66.7 mM | 0 mM |
| 1.20 | 66.7 mM | 80 mM | 0 mM |
| 2.00 | 66.7 mM | 66.7 mM | 66.7 mM |

Reactions took place in a manner similar to that described above. The concentration of the reactants was half of that used for Sample Sets A, B, and C. Four rounds of settle/decant were performed during buffer exchange into 0.9% saline. Each round of settle/decant involved diluting 50 mL of precipitated aluminum adjuvant suspension with about 1 liter of 0.9% saline, mixing, waiting for the suspension to settle, then removing about 1 liter of clear supernatant. Buffer exchange for Sample Set D was conducted at room temperature over a period of more than a month. Autoclaving was with a liquids cycle for 60 minutes at 121° C.

Set E

The aluminum phosphate adjuvant precipitation reaction by a co-mix method was performed 5 times independently with the same target reaction parameters. The phosphate/ aluminum molar ratio of the reactant solutions was 2.2, and the phosphate solution was sodium phosphate dibasic, pH 9 (not adjusted). The target concentration of aluminum in the aluminum chloride reactant solution was 1.8 mg aluminum/mL. The table below describes how the 5 aluminum chloride hexahydrate reactant solutions and the 5 sodium phosphate dibasic reactant solutions were prepared.

TABLE 6

Preparation details for sample set "E".

| Grams of sodium phosphate dibasic (FW 141.96 g/mol) dissolved in 1 liter of water to prepare phosphate reactant solution | Grams of aluminum chloride hexahydrate (FW 241.43 g/mol) dissolved in 600 mL of water to prepare aluminum reactant solution |
|---|---|
| 20.8470 | 9.6752 |
| 20.8316 | 9.6791 |
| 20.8484 | 9.6655 |
| 20.8420 | 9.6684 |
| 20.8308 | 9.6598 |

60 mL syringes were loaded with the reactant solutions, and co-mixed through a small plastic static in-line mixer, into a rapidly stirred container. The total flow rate into the container was 1 mL/second. Stirring continued for 5 minutes after addition was complete. Buffer exchange was similar to that done for Sample Sets A, B, C, and D. Autoclaving was with a liquids cycle for 60 minutes at an average temperature of 123° C., two degrees higher than for the other sample sets.

For the precipitation reactions, in summary, a general procedure employed during this lab scale reaction space screening was to co-mix aluminum chloride hexahydrate solution (1.8 mg/mL to 3.6 mg/mL) with a 1:1 volume of a sodium phosphate solution. The molar ratio of phosphate in the phosphate reactant solution, to aluminum in the aluminum reactant solution, ranged from 1.0 to 4.0. The pH of the sodium phosphate solutions ranged from >12 to 7.4. Phosphate solutions were prepared from individual sodium phosphate compounds (sodium phosphate dibasic, sodium phosphate tribasic), or from mixtures of sodium phosphate compounds (sodium phosphate monobasic+sodium phosphate dibasic, sodium phosphate dibasic+sodium phosphate tribasic), or from sodium phosphate compounds with additional base (sodium hydroxide) added. Reactants were co-mixed either by running the two reactant streams together (i.e. through a static in-line mixer), or by not running the two reactant streams directly together, but rather adding them separately to the same stirred container. Buffer exchange into 0.9% sodium chloride was achieved by different numbers of "settle/decant" cycles. Samples were analyzed both before and after autoclaving. When autoclaved, conditions were for 60 minutes at an average temperature of 121-123° C.

pH measurements were made on IQ240 pH meters using stainless steel probes. Generally, two pH measurements were made using two different meters/probes, and the average of the two pH measurements was reported.

PZC measurements were made by diluting the aluminum containing adjuvant to approximately 15 µg/ml in a 20 mM TRIS:Acetate buffer. Several separate TRIS:acetate buffers were used to cover a pH range of 4.0-8.0, typically in increments of 1.0 pH units. Then the zeta potential was measured using a Zetasizer instrument. The data were plotted as pH (x-axis) vs. zeta potential (y-axis), and the x intercept was calculated, which gave the point of zero charge.

ICP measurements were made on both the supernatant and the solids fraction of the aluminum containing adjuvants to get phosphorous and aluminum concentrations. Ten milliliters of each sample were placed in 15 mL conical tubes and centrifuged at approximately 2000 rcf. The supernatant was removed and tested for phosphorous and aluminum concentration. The pellet of aluminum containing adjuvant was then resuspended to 10 mL with 0.9% sodium chloride solution and tested for phosphorous and aluminum concentration. The supernatant concentrations were used to see if the reaction was going to completion and the amount of excess phosphate in solution. The pellet analysis was used to calculate the molar P/Al (phosphate to aluminum) ratio in the solids that resulted from the specific reaction conditions.

FIGS. 1-5 are reaction space plots in which the contours were generated from a surface fit to the data. Based on results from many samples, these plots show predicted values for pH, PZC, and P/Al ratio as a function of two reaction parameters (phosphate:aluminum molar ratio of the reactant solutions, and pH of the phosphate-containing solution). These plots allow prediction of how to achieve target properties of an aluminum adjuvant produced by the methods of this invention, and served as a guide during scale-up of the production process. The lab scale work suggested that this method of aluminum phosphate production would be well suited to design and control in a manufacturing setting.

Example 2

Comparison of Aluminum Phosphate Adjuvant Made by Co-Mixing or by a Batch Precipitation Method Co-mixing has certain theoretical advantages over batch precipitation of aluminum phosphate adjuvant. To understand what differences might be encountered compared to a batch process, lab-scale comparison studies between the co-mix and batch precipitation methods were performed.

Six samples of aluminum phosphate were prepared by a co-mix method and six samples were prepared by a batch method. The batch method involved filling a mixing container with all the aluminum chloride reactant solution, and adding the sodium phosphate reactant solution to the container over time. Numerous precautions were taken to ensure the validity of the comparison. These included making corresponding "co-mix" and "batch" samples on the same occasion, making the samples with the same reagents, making the samples using the same equipment, analysis of both sets of samples performed on the same occasion and using the same instruments and methods.

The aluminum reactant solution was prepared at 4.2 grams aluminum/mL by dissolving aluminum chloride hexahydrate in water (37.58 grams aluminum chloride hexahydrate/liter). The target molar ratio of phosphate to aluminum for the reactant solutions was 3:1. The target pH of the phosphate reactant solutions was 8.0. To achieve that target molar ratio and pH, solutions of 0.467 M sodium phosphate dibasic (66.3 grams/liter) and 0.467 M sodium phosphate monobasic monohydrate (64.4 grams/liter) were prepared. While monitoring the pH with a pH meter, a smaller volume of sodium phosphate monobasic solution was added to a larger volume of sodium phosphate dibasic solution until pH 8.0 was achieved. Sodium phosphate monobasic solution contributed less than about 5% of the final volume of the phosphate reactant solutions. After reaction in a 1:1 volume ratio of the aluminum and phosphate reactant solutions, the final concentration of aluminum in the aluminum phosphate adjuvant suspension was 2.1 grams aluminum/mL.

To prepare samples by the co-mix method, two peristaltic pumps operating at the same flow rate delivered the reagent solutions into a 2 L beaker, which was stirred at a medium speed with a 7.2 cm stir bar. The flow rate for each pump was 10.7 mL/min and pumping ran for 20 minutes (with stirring throughout), resulting in about 428 mL of adjuvant suspension. Stirring was continued for about 10 minutes after pumping was stopped.

To prepare the samples by the batch precipitation method, the only modification to the co-mix method was that the whole volume of aluminum chloride solution that would have been dispensed over 20 minutes (214 mL) was added to the beaker at the beginning of the run, and only the pump that delivered the sodium phosphate solution was operating during the 20 minute dispense period. Mixing continued about 10 minutes beyond the completion of pumping, as above.

Both "co-mix" and "batch" preparation method samples were buffer exchanged into 0.9% sodium chloride solution by repeated cycles of resuspension in saline, settling of the aluminum adjuvant solids, and removal of the solids-free supernatant ("settle/decant"). Measurements were made on the samples before and after autoclaving. Autoclaving followed our typical lab-scale condition of using a liquids cycle for 1 hour at 121° C.

The resulting 12 samples (6 co-mix, 6 batch) were analyzed for pH, Zeta potential PZC, and final P/Al ratio, to characterize the consistency of each method and differences between the two methods. The co-mix method appears to have a consistency advantage over the batch method tested, as seen by comparing standard deviation of mean results from each method.

TABLE 7 pH measurements for co-mix and batch samples, average ± standard deviation.

|  | Before buffer exchange | After buffer exchange, not autoclaved | After buffer exchange and after autoclaving |
|---|---|---|---|
| Batch method | 6.23 ± 0.04 | 5.85 ± 0.15 | 5.24 ± 0.16 |
| Co-mix method | 5.97 ± 0.03 | 5.91 ± 0.02 | 5.41 ± 0.05 |
| N = | 5 | 6 | 6 |

Figure 6:
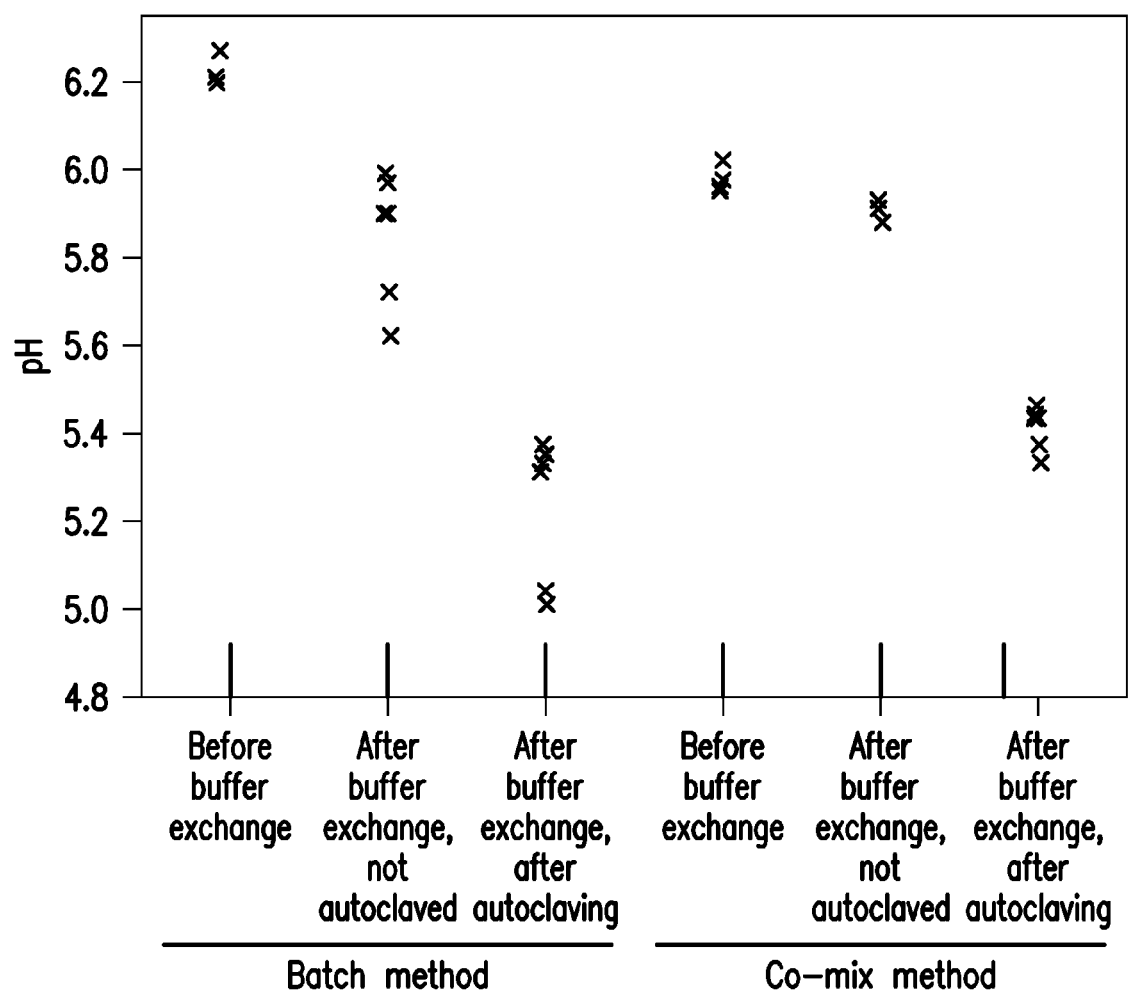
FIG. 6. Comparison of pH measurements for "batch" and "co-mix" manufactured adjuvant samples.

FIG. 6 is a graphical comparison of pH measurements for batch and co-mix samples. The pH of the samples prepared by the batch method were found to drift downward between preparation and autoclaving to a much larger extent than the co-mixed samples. Therefore, it appears that there is both a pH stability and pH consistency advantage with using the co-mix method.

The zeta potential PZC of the 12 samples was measured before and after autoclaving. As with the case for pH, samples prepared by the co-mix method were more consistent than those prepared by the batch method.

Figure 7A:
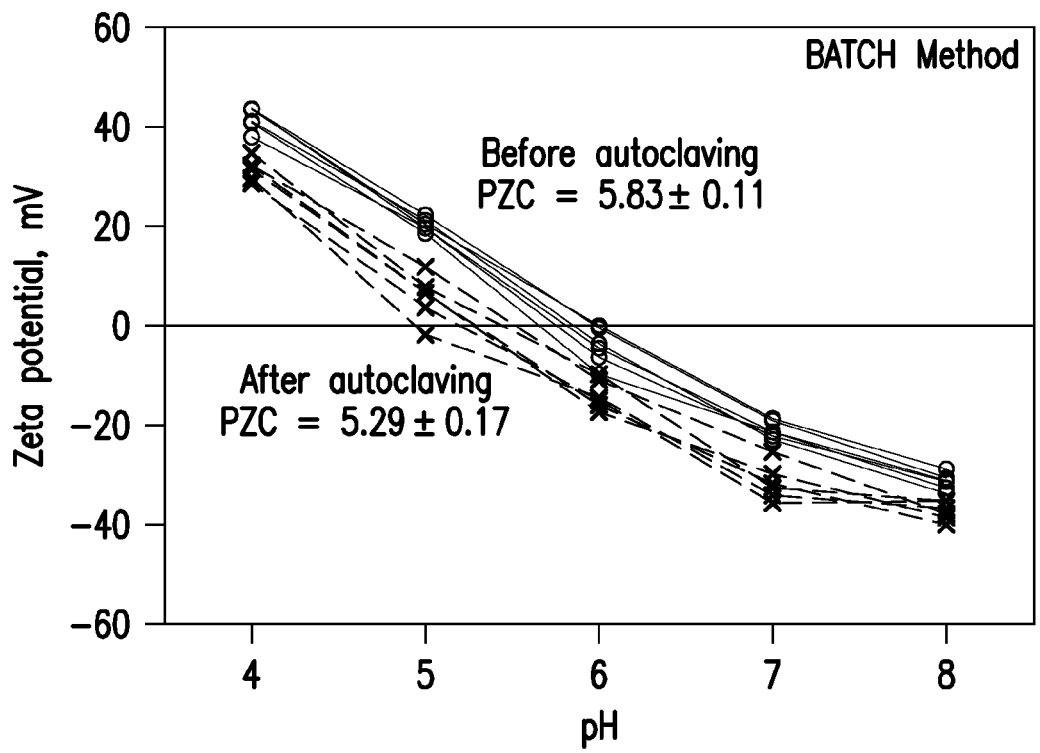
FIGS. 7A-B. Comparison of zeta potential PZC (point of zero charge) measurements for (A) "batch" and (B) "co-mix" manufactured adjuvant samples.
Figure 7B:
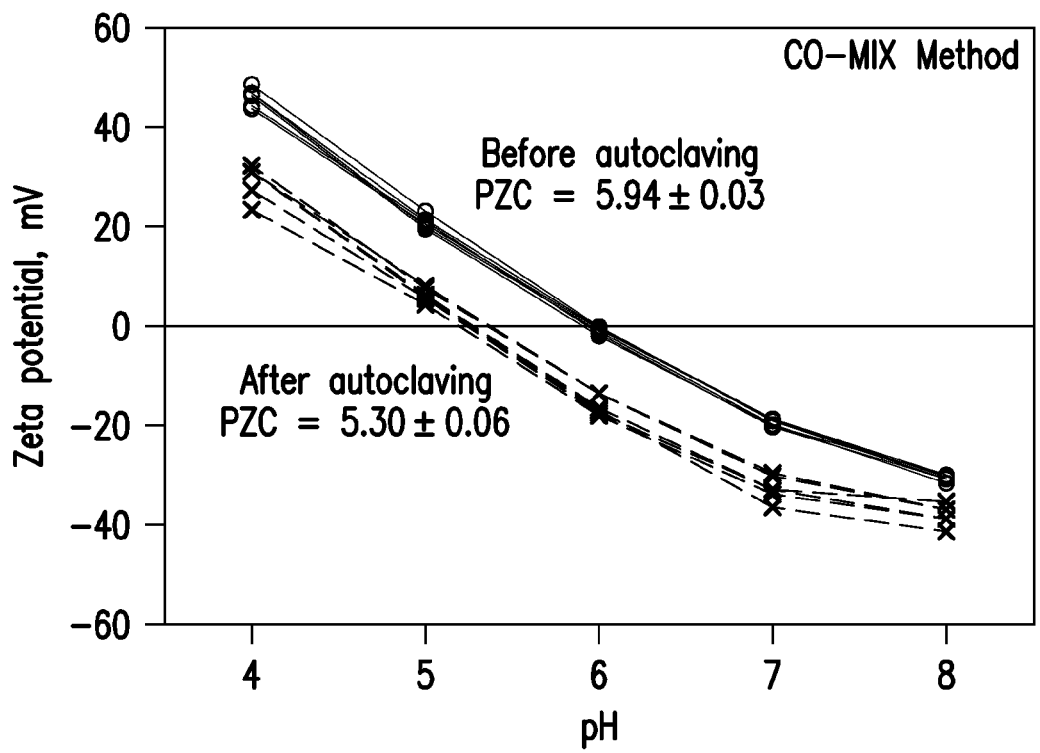

FIGS. 7A-B are a graphical comparison of zeta potential PZC (point of zero charge) measurements for batch and co-mix samples, including mean and standard deviation for results obtained from each method.

The molar ratio of phosphorous to aluminum in the precipitated solids has a larger change upon autoclaving for the batch samples than for the co-mix samples. The co-mix samples appear slightly more consistent by the measure of this assay. Table 8 lists the average P/Al molar ratio from 6 samples by each method, ±standard deviation.

TABLE 8

P/Al molar ratios of aluminum phosphate solids produced by different methods.

|  | Post buffer exchange, before autoclaving | buffer exchange, after autoclaving |
|---|---|---|
| Batch method | 1.03 ± 0.04 | 0.85 ± 0.06 |
| Co-mix method | 1.03 ± 0.03 | 0.94 ± 0.01 |
| N = | 6 | 6 |

The data from this lab-scale comparison supports the idea that the co-mix method is better than the batch method for preparing aluminum phosphate adjuvant with consistent pH, PZC, and P/Al molar ratio in the precipitated solids.

Example 3

Pilot-Scale Aluminum Phosphate Adjuvant Manufacture

This example describes a pilot-scale process for routine manufacturing of small batches of Aluminum Phosphate Adjuvant (APA).

(1) Raw materials used in this process are summarized in Table 9 below:

TABLE 9

Raw Materials and Solutions used for APA Manufacturing

| Raw Material/Solution | Purpose |
|---|---|
| Aluminum Chloride (hexahydrate) | Reactant |
| Sodium Phosphate Dibasic (anhydrous) | Reactant |
| Sterile distilled water | Solvent, Diluent |
| Water for Injection (WFI) | UF filter flushing |
| 0.5N Sodium Hydroxide | UF filter sanitization |
| 0.9% Sodium Chloride | Diafiltration buffer |

(2) The aluminum chloride reactant (156 mM Al) was prepared as follows. A clean 5 L glass bottle with 3-inch magnetic stir bar was tared on a bench top scale with magnetic stir plate. About 4000 g of sterile distilled water was charged into the bottle. A target of 187.9 g of aluminum chloride (hexahydrate) was charged to the vessel and mixed until the solids were dissolved. While stirring, sterile distilled water was added to reach a target net weight of 5050 g. The aluminum chloride solution was stored at room temperature until further processing.

(3) The sodium phosphate reactant (390 mM Phosphate) was prepared as follows. A clean 10 L glass bottle with 3-inch magnetic stir bar was tared on a bench top scale with magnetic stir plate. About 5000 g of sterile distilled water was charged into the bottle. A target of 331.5 g of Sodium phosphate dibasic (anhydrous) was charged to the vessel and mixed until the solids were dissolved. While stirring, sterile distilled water was added to reach a target net weight of 6251 g. The sodium phosphate solution was filtered through a Millipak-60 0.22 µm sterilizing grade filter to remove particulates and ensure low bioburden. The sodium phosphate solution was stored at room temperature until further processing.

(4) A T-mixing setup was constructed by connecting two lengths of 3/16" silicone tubing and one length of 3/8" silicone tubing to a 5/16" "T" as shown below. Each length of 3/16"

tubing was threaded through an appropriately sized peristaltic pump. A clean 10 L glass vessel with 3-inch stir bar was tared on a bench top scale with magnetic stir plate. The outlet of the ⅜" tubing was directed into the clean glass bottle, while the inlets of the 3/16" tubing lengths were placed in the aluminum chloride and sodium phosphate reactant solutions as shown in the schematic below.

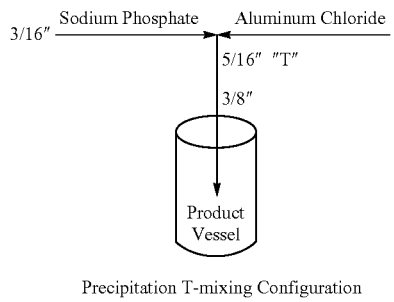

Precipitation T-mixing Configuration (5) Each of the peristaltic pumps were set to 600 mL/min and the lines were primed up to the 5/16" "T". Upon completion of priming, the two pumps were simultaneously turned on to begin T-mixing precipitation. Once the height of the fluid in the collection vessel was above the stir bar, mixing in the collection vessel was initiated. The pumps were simultaneously turned off when the collection vessel reached a target net weight of 7070 g. The precipitated intermediate was mixed for about 10 minutes following T-mixing and sampled prior to the next step.

(6) A Silverson L4RT-A High Shear Mixer with a 1.25" diameter rotor and square hole high-shear stator was used for the size-reduction step. The purpose of the size-reduction step is to ensure a consistent and uniform aggregate particle size distribution within the target size range. The size reduction step was carried out by recirculating the product through the Silverson mixer for 120 minutes at a mixing speed of 8000 RPM. Mixing in the product vessel was maintained with a stir bar throughout the process and ½" silicone tubing was used for all connections between the Silverson mixer and the product vessel. The size-reduced intermediate was sampled and stored at 2-8° C. until further processing.

(7) The net weight of the size-reduced intermediate input to the ultrafiltration (UF) step was 6923 g. After removal from cold storage, the product was mixed for 90 minutes to resuspend the product and allow equilibration to room temperature. A UF system was set-up using a Millipore Pellicon-2 Miniholder filter housing (Catalog No. XX42PMINI) and 2×0.1 m² Millipore 300 kD Biomax PES filters (cat# P2B300V01) for a total filter area of 0.2 m². ¾" pressure gauges were installed on the permeate, feed, and retentate ports of the filter holder to monitor transmembrane pressure (TMP) and pressure drop (ΔP) throughout the process. A ¾" manual retentate control valve was installed downstream of the retentate pressure gauge. Appropriately sized sanitary tubing was used to connect the filter holder to the product, permeate, UF buffer, and flush vessels as needed. Peristaltic pumps were utilized to control feed flowrate and permeate flowrate.

(8) Following installation, the UF system was flushed with WFI per standard procedures and the system was integrity tested to ensure the absence of gross leaks in the system. The filters were then sanitized with 0.5 N NaOH by first flushing about 2 L through the retentate and permeate at a feed flowrate of about 1000 mL/min and retentate pressure of about 1 psig. Next, another 2 L were recirculated through the retentate and permeate at a feed flowrate of 1000 mL/min and retentate pressure of about 1 psig for 30 minutes. Following sanitization, the filters were again flushed with WFI using standard procedures until the retentate and permeate effluent reached approximately neutral pH.

(9) Following filter preparation, the product was concentrated about 2× by directing the permeate to a collection vessel and setting feed flowrate to 2400 mL/min and permeate flowrate to 83 mL/min. Retentate pressure was consistently controlled at about 5 psig using the retentate pressure control valve. After concentration, diafiltration was initiated by beginning addition of UF buffer (0.9% sodium chloride) to the product vessel at the same flowrate as the permeate is output from the system. A 6 diavolume buffer exchange was completed by monitoring net weight of permeate collected and stopping the process at the appropriate weight. The product vessel was mixed with a stir bar throughout concentration and diafiltration.

(10) Product hold-up was recovered from the filters by conducting a UF buffer flush upon completion of diafiltration. This was done by flushing 1250 g of fresh 0.9% sodium chloride through the feed/retentate into the product vessel at about 1000 mL/min with the permeate line clamped. The diafiltered product intermediate was mixed for 5 minutes before sampling and proceeding to the next step. The net weight of the diafiltered intermediate was 4265 g.

(11) The diafiltered intermediate was resuspended and dispensed in 200 mL aliquots into clean 1 L glass bottles for steam sterilization. The batch yielded 21 bottles of about 200 mL diafiltered product per bottle output from the dispensing step.

(12) The 21×1 L product bottles were sterilized in an "Open Container" steam autoclave cycle for 62 minutes at 123° C. Product bottles were removed from the autoclave immediately upon completion of the cycle, allowed to equilibrate to room temperature, and then stored at 2-8° C.

After the manufacture of Aluminum Phosphate Adjuvant (APA) at pilot scale, the material was characterized by several analytical methods. Table 10 is a summary of these results.

TABLE 10

Properties of Pilot-Scale APA

| Property | Method | Result |
| --- | --- | --- |
| Aluminum concentration | Inductively Coupled Plasma Spectroscopy (ICP) | 2.9 mg/mL as Aluminum |
| Phosphate to Aluminum Molar Ratio (P/Al, adjuvant solids only) | ICP | 1.02 |
| pH | pH | 5.39 |
| Point of Zero Charge (PZC) | Zeta Potential | 5.23 |
| Aggregate Particle Size | d(v, 0.5) by Static Light Scattering (SLS) | 3.97 μm |

TABLE 10-continued

Properties of Pilot-Scale APA

| Property | Method | Result |
| --- | --- | --- |
| Free Phosphate | Malachite Green Phosphate Assay | 18.0 mM |
| Sodium Chloride | Chloride by Silver Nitrate Titration converted to % Sodium Chloride | 0.97% |

All results were within the desired ranges.

Example 4

Commercial-Scale Aluminum Phosphate Adjuvant Manufacture

This example describes a commercial-scale process for routine manufacturing of Aluminum Phosphate Adjuvant (APA).

(1) Raw materials used in this process are summarized in Table 11 below.

TABLE 11

Raw Materials and Solutions used for APA Manufacturing

| Raw Material/Solution | Purpose |
| --- | --- |
| Aluminum Chloride (hexahydrate) | Reactant |
| Sodium Phosphate Dibasic (anhydrous) | Reactant |
| Water for Injection (WFI) | Solvent, Diluent, UF filter flushing |
| Sodium Chloride | Diafiltration buffer |

(2) Major equipment/materials used in this process are summarized in Table 12.

TABLE 12

Equipment and Materials used for APA Manufacturing

| Equipment/Materials | Purpose |
| --- | --- |
| ATMI Newmix Pad-Drive 1000 Mixing System with Q-mix stainless steel containers and 200 L and 1000 L disposable bags | Reactant and UF Buffer Manufacture |
| Jacketed 250 L tank with incoming air filter and vent filter | Product Vessel, In-situ sterilization |
| Rotary Lobe Pump | Recirculation during Ultrafiltration and Size Reduction |
| Silverson 275UHS High-Shear Mixer | Particle Size Reduction |
| Millipore CUF-1 Filter Holder and Cart | Ultrafiltration |
| Millipore Pellicon 2 Biomax PES Ultrafilters, 300 kD | Ultrafiltration |
| Peristaltic Pumps | Reactant T-mixing, UF Buffer Addition, UF Permeate Flow |
| Floor scale | Measuring quantity of dispensed product |
| 45 L glass bottles | Product storage |

(3) The aluminum chloride reactant (156 mM Al) was prepared as follows. An ATMI Newmix Pad-Drive 1000 Mixing System equipped with a paddle mixing agitation device was used for this process. A clean 200 L disposable bag was loaded onto a 200 L Q-mix stainless steel container. About 145.9 kg of WFI was charged into the bag. A target of 5.65 kg of aluminum chloride (hexahydrate) was charged to the bag and mixed for about 60 minutes at a rotational speed of 65 with paddle alternation on (30 second intervals) using a 20 degree paddle angle. Dissolution of the aluminum chloride was visually confirmed at the completion of mixing. Samples were taken from the aluminum chloride solution prior to further processing. The pH of the aluminum chloride reactant solution measured 3.02 and the conductivity measured 35.6 mS/cm. The aluminum chloride solution was stored at room temperature until further processing.

(4) The sodium phosphate reactant (390 mM Phosphate) was prepared as follows. An ATMI Newmix Pad-Drive 1000 Mixing System equipped with a paddle mixing agitation device was used for this process. A clean 200 L disposable bag was loaded onto a 200 L Q-mix stainless steel container. About 148.3 kg of WFI was charged into the bag. A target of 8.30 kg of sodium phosphate dibasic (anhydrous) was charged to the bag and mixed for about 60 minutes at a rotational speed of 65 with paddle alternation on (30 second intervals) using a 20 degree paddle angle. Dissolution of the sodium phosphate was visually confirmed at the completion of mixing. Samples were taken from the sodium phosphate solution prior to further processing. The pH of the sodium phosphate solution measured 8.96 and the conductivity measured 36.8 mS/cm. The sodium phosphate solution was stored at room temperature until further processing.

(5) The sodium chloride ultrafiltration buffer (0.9% w/v) was prepared as follows. An ATMI Newmix Pad-Drive 1000 Mixing System equipped with a paddle mixing agitation device was used for this process. A clean 1000 L disposable bag was loaded onto a 1000 L Q-mix stainless steel container. About 996 L of WFI was charged into the bag. A target of 9.00 kg of sodium chloride was charged to the bag and mixed for about 60 minutes at a rotational speed of 65 with paddle alternation on (30 second intervals) using a 20 degree paddle angle. Dissolution of the sodium chloride was visually confirmed at the completion of mixing. The pH of the sodium chloride solution measured 5.85 and the conductivity measured 15.67 mS/cm. The sodium chloride solution was stored at room temperature until further processing.

(6) T-mixing of the aluminum chloride and sodium phosphate reactants was performed by pumping each of the solutions through peristaltic pumps at a flow rate of 3.0 L/min per solution. T-mixing was carried out under controlled room temperature conditions, ensuring the starting product reactants were within 17-33° C. prior to starting the process. Each of the solutions were filtered through 0.22 µm filters for bioburden and particulate reduction then directly impinged upon each other at a "T" in ½" (nominal) piping with an inside diameter of 0.37". The process was automated such that the initial T-mixed product was directed to drain until reactant flowrates were confirmed to be well controlled and stable. The resulting precipitated aluminum hydroxyphosphate intermediate was then collected in a 250 L tank. The agitator of the tank was turned on to a speed of 50 RPM when the product in the tank had reached a weight of 25 kg. The agitator speed was increased to a speed of 140 RPM when the product in the tank reached a weight of 50 kg. The peristaltic pumps were stopped when the tank net weight had reached 200 kg. The amount of sodium phosphate and aluminum chloride that had been T-mixed and added to the product vessel was 99.0 L and 99.1 L, respectively. The volumetric ratio of sodium phosphate to aluminum chloride reacted was therefore 0.999. The tank agitator remained on for 10 minutes after T-mixing to ensure the product intermediate was homogeneous before proceeding to the next process step. Product samples were taken at the completion of this step. The product intermediate was held for about 25.5 hrs with the agitator off before proceeding to the next step.

(7) A Silverson 275UHS High Shear Mixer with a 2.75" diameter rotor and square hole high-shear stator was used for the size reduction step. The product was first resuspended for 45 minutes at an agitator speed of 140 RPM. The size reduction step was then carried out by recirculating the product through the Silverson mixer for 125 volumetric turnovers at a high-shear mixer speed of 3600 RPM. A recirculation flow rate of about 90 L/min was utilized to ensure appropriate pressure at the inlet (about 0.48-0.52 barg) and outlet (about 0.59-0.64 barg) of the high-shear mixer. The rotary lobe pump was run at about 128 RPM to obtain this flow rate, which resulted in a processing time of about 4 hours and 20 minutes to achieve the target number of turnovers for this particular batch. Mixing in the product vessel was maintained during the size reduction operation by running the agitator at 140 RPM. Product temperature was controlled to 17-33° C. during the size reduction step by input of chilled water to the tank jacket to mitigate any temperature increase due to energy input by the high-shear mixer and rotary lobe pump. Product samples were taken during and upon completion of this step. The product intermediate was held for about 24 hrs with the agitator off before proceeding to the next step.

(8) The UF equipment consisted of a Millipore CUF-1 filter holder/cart with 4×2 $m^2$ Pellicon 2 300 kD Biomax PES filters (cat# P2B300V20) for a total filter area of 8 $m^2$. Pressure transmitters on the permeate, feed, and retentate streams were used to monitor transmembrane pressure (TMP) and pressure drop ($\Delta P$) throughout the process. A rotary lobe pump was used to control retentate flowrate and peristaltic pumps were used to control permeate and buffer addition flowrates.

(9) The UF system was flushed with WFI per standard procedures prior to use. Since this particular batch was not destined for human use, sanitization of the UF filters was not required. For a batch intended for human use, 0.1 N or 0.5 N NaOH solution would be used for sanitization per standard procedures.

(10) The net weight of the size-reduced intermediate input to the ultrafiltration (UF) step was 183.0 kg. Prior to UF, the product was first resuspended for 45 minutes using an agitator speed of 140 RPM. Product was then continually agitated during the UF process at 140 RPM to maintain homogeneity. Following filter flush, the product was concentrated about 1.5×. The process started by beginning recirculation through the filters with retentate flow at 97.3 L/min (730 L/($m^2$-hr)) with the permeate valve closed. Retentate pressure was consistently about 0.70-0.73 barg during the process and did not require control. Once retentate had reached the target flow rate, the permeate valve was opened and the permeate flow rate was slowly ramped up to 4.0 L/min over the course of about 10 minutes. The endpoint of concentration was determined by net product weight. At that time, diafiltration was initiated by beginning addition of UF buffer (0.9% sodium chloride) to the product vessel at the same flow rate as the permeate was output from the system (4.0 L/min). A 6.0 diavolume buffer exchange was completed using totalized permeate flow rate to determine the endpoint. TMP ranged between 0.04 and 0.14 barg during concentration and between 0.14 and 0.26 barg during diafiltration. Pressure drop ($\Delta P$) ranged between 1.04 and 1.12 barg during concentration and between 1.12 and 1.20 barg during diafiltration. Product temperature was controlled to 17-33° C. during the ultrafiltration step by input of chilled water to the tank jacket to mitigate any temperature increase due to energy input by the rotary lobe pump.

(11) Product hold-up was recovered from the filters by conducting a UF buffer flush upon completion of diafiltration. This was done by flushing 10 L of fresh 0.9% sodium chloride through the feed/retentate into the product vessel at about 5.7 L/min with the permeate line closed. The diafiltered product intermediate was then sampled at the completion of this step. The net weight of the diafiltered intermediate was 130.6 kg. The product intermediate was held for about 24.5 hrs with the agitator off before proceeding to the next step.

(12) The diafiltered intermediate was resuspended for 45 minutes using an agitator speed of 140 RPM. The product was then steam sterilized in the following manner. Steam was applied to the vessel jacket to heat the product to about 121° C. At that time steam was also injected into the vessel headspace to facilitate the remaining heating, help remove air from the headspace, and ensure complete sterilization of internal tank components. The product was then heated to a target dwell temperature of 124° C. and maintained at this temperature for 24 minutes. Total heat-up time from ambient temperature to dwell temperature was 32 minutes. Upon completion of dwell, the product was cooled to about 22° C. by recirculating chilled water through the tank jacket. Cooling the product from 124° C. to under 30° C. took about 30 minutes. The product was mixed throughout the sterilization cycle at an agitator set point of 140 RPM. Following sterilization, the product net weight was 124.8 kg. The sterilized bulk product was sampled at the completion of this step. The sterilized product was held for about 72.5 hrs with the agitator off before proceeding to the next step.

(13) The sterilized product was resuspended for 45 minutes using an agitator speed of 140 RPM. The product was dispensed into 4×45 L glass bottles for storage. Final product samples were taken from each of the product bottles immediately after the bottles were filled.

After the manufacture of Aluminum Phosphate Adjuvant (APA) at commercial scale, the material was characterized by several analytical methods. Table 13 is a summary of these results.

TABLE 13

| Properties of Commercial-Scale APA | | |
|---|---|---|
| Property | Method | Result |
| Aluminum concentration | Inductively Coupled Plasma Spectroscopy (ICP) | 2.8 mg/mL as Aluminum |

TABLE 13-continued

Properties of Commercial-Scale APA

| Property | Method | Result |
|---|---|---|
| Phosphate to Aluminum Molar Ratio (P/Al, adjuvant solids only) | ICP | 0.95 |
| PH | pH | 5.26 |
| Point of Zero Charge (PZC) | Zeta Potential | 5.15 |
| Aggregate Particle Size | d(v, 0.5) by Static Light Scattering (SLS) | 6.98 μm |
| Free Phosphate | Malachite Green Phosphate Assay | 13.1 mM |
| Sodium Chloride | Chloride by Capillary Electrophoresis (CE) converted to % Sodium Chloride | 0.92% |

All results were within the desired ranges.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method for the preparation of aluminum hydroxyphosphate adjuvant comprising the steps of:
   (a) co-mixing a solution of an aluminum salt with a solution of a phosphate at a defined P/Al molar ratio to precipitate aluminum hydroxyphosphate adjuvant in the presence of a buffer that maintains a constant pH, wherein said co-mixing involves the simultaneous and continuous combining of the solution of an aluminum salt and the solution of a phosphate and the defined P/Al ratio is in the range of 2.0-3.5; and
   (b) buffer exchanging with a buffer exchange solution to remove at least 80% of any excess phosphate, buffer or other residual salts from the original reactants.

2. The method of claim 1, wherein the solution of phosphate is selected from the group consisting of sodium phosphate monobasic, sodium phosphate dibasic, sodium phosphate tribasic, phosphoric acid, potassium phosphate monobasic, potassium phosphate dibasic, potassium phosphate tribasic, ammonium phosphate monobasic, ammonium phosphate dibasic, ammonium phosphate tribasic, ammonium sodium phosphate, and combinations thereof.

3. The method of claim 1, wherein the solution of phosphate has a pH from 7.4 to 12.4, 8.0 to 10.0, or 8.5 to 9.5.

4. The method of claim 1, wherein the solution of phosphate comprises sodium phosphate dibasic.

5. The method of claim 1, wherein the aluminum salt is selected from the group consisting of aluminum chloride, potassium aluminum sulfate, aluminum ammonium sulfate, aluminum nitrate, aluminum bromide, aluminum bromate, aluminum chlorate, aluminum iodide, and different hydrate forms of these.

6. The method of claim 5, wherein the aluminum salt is aluminum chloride hexahydrate.

7. The method of claim 1, wherein the aluminum hydroxyphosphate adjuvant has one or more of the following properties:
   zeta potential Point of Zero Charge (PZC) from 4.2 to 6.9, from 4.7 to 6.4, or 4.7 to 5.4;
   aggregate particle size volume median diameter, d(v,0.5), less than 40 microns, from 2 to 10 microns, or from 3 to 6 microns;
   pH in the range of 3.0 to 8.0, 4.5 to 7.2, or 4.5 to 5.5; or
   P/Al molar ratio measured in the precipitated aluminum hydroxyphosphate adjuvant of 0.6-1.2; 0.8-1.2 or 0.9-1.1.

8. The method of claim 7, further comprising performing size reduction prior to step (b) to reduce the aggregate particle size volume median diameter (d(v,0.5)) from about 10 to 40 microns to about 2 to 10 microns or 3 to 6 microns.

9. The method of claim 8, wherein performing the size reduction is by use of a high-shear rotor-stator mixer, vigorous mixing with an impeller, or recirculating through a pump.

10. The method of claim 1, wherein the buffer exchange solution for buffer exchanging is saline or histidine.

11. The method of claim 1, wherein the buffer exchange step is carried out by ultrafiltration.

12. The method of claim 11, wherein the extent of ultrafiltration buffer exchange is 4 to 15 diavolumes or 5 to 7 diavolumes.

13. The method of claim 1, further comprising sterilizing the aluminum hydroxyphosphate adjuvant after step (b).

14. The method of claim 13, wherein said sterilizing is by autoclaving or in-situ steam sterilization.

\* \* \* \* \*